(12) United States Patent
Izui et al.

(10) Patent No.: US 7,208,296 B2
(45) Date of Patent: Apr. 24, 2007

(54) METHOD FOR PRODUCING L-GLUTAMIC ACID BY FERMENTATION ACCOMPANIED BY PRECIPITATION

(75) Inventors: Hiroshi Izui, Kawasaki (JP); Mika Moriya, Kawasaki (JP); Seiko Hirano, Kawasaki (JP); Yoshihiko Hara, Kawasaki (JP); Hisao Ito, Kawasaki (JP); Kazuhiko Matsui, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/150,265

(22) Filed: Jun. 13, 2005

(65) Prior Publication Data

US 2005/0227334 A1    Oct. 13, 2005

Related U.S. Application Data

(63) Continuation of application No. 09/641,892, filed on Aug. 18, 2000, now Pat. No. 7,015,010.

(30) Foreign Application Priority Data

Aug. 20, 1999  (JP) .................... 11-234806
Mar. 21, 2000  (JP) .................... 2000-78771

(51) Int. Cl.
*C12P 13/14* (2006.01)
*C12N 15/00* (2006.01)
*C12N 1/20* (2006.01)
*C12N 1/36* (2006.01)
*C12N 15/63* (2006.01)

(52) U.S. Cl. ....................... 435/110; 435/106
(58) Field of Classification Search ............... None
See application file for complete search history.

(56) References Cited

U.S. PATENT DOCUMENTS

| 3,032,474 | A | 5/1962 | Foster et al. |
| 3,220,929 | A | 11/1965 | Kinoshita et al. |
| 5,908,768 | A | 6/1999 | Ono et al. |
| 6,331,419 | B1 | 12/2001 | Moriya et al. |
| 6,596,517 | B2 | 7/2003 | Izui et al. |
| 6,653,110 | B2 | 11/2003 | Sato et al. |
| 2001/0019836 | A1 | 9/2001 | Moriya et al. |
| 2002/0192772 | A1 | 12/2002 | Sato et al. |
| 2003/0003550 | A1 | 1/2003 | Nakamura et al. |
| 2003/0119153 | A1 | 6/2003 | Moriya et al. |

FOREIGN PATENT DOCUMENTS

| EP | 0 636 695 | 2/1995 |
| EP | 0 670 370 | 9/1995 |
| EP | 0 952 221 | 10/1999 |
| JP | 62-288 | 1/1987 |
| WO | WO 97/08294 | 3/1997 |

OTHER PUBLICATIONS

Kwe-Chao Chao, et al., vol. 77, pp. 715-725, "A Glutamic Acid-Producing *Bacillus*", Nove. 10, 1958.
R.M. Borichewski, Journal of Bacteriology, vol. 93, No. 2, pp. 597-599, "Keto Acids as Growth-Limiting Factors in Autotrophic Growth of Thiobacillus Thiooxidans", Feb. 1967.
Abstract of Crit. Rev. Biotechnol., vol. 15, No. 1, pp. 73-103, "Recent Advances in the Physiology and Genetics of Amino Acid-Producing Bacteria", 1995.
Bailey. Toward a science of metabolic engineering. Science 252: 1668-1675, 1991.
WPI/DERWENT Abstract, "Manufacturing L-Glutamic Acid by Fermentation for Foodstuff, Pharmaceutical—Comprises Culturing Corynebacterium Striatum in Culture Medium", JP11009296, Jan. 19, 1999, AN 1999-169864.
J. Mergaert, et al., "Transfer of *Erwinia ananas* (Synonym, *Erwinia uredovora*) and *Erwinia stewartii* to the Genus *Patonea* Emend. as *Pantoea ananas* (Serrano 1928) Comb. Nov. and *Pantoea stewartii* (Smith 1898) Comb. Nov., Respectively, and Description of *Pantoea stewartii* Subsp. *Indologenes* Subsp. Nov.", International Journal of Systematic Bacteriology, vol. 43, No. 1, Jan. 1993, pp. 162-173.
S.-W. Kwon, et al., "Phylogenetic Analysis of *Erwinia* Species Based on 16S RRNA Gene Sequences", International Journal of Systematic Bacteriology, vol. 47, No. 4, Oct. 1997, pp. 1061-1067.
Kwei-Chao Chao, et al., vol. 77, pp. 715-725, "A Glutamic Acid-Producing *Bacillus*", Nov. 10, 1958.

*Primary Examiner*—David Guzo
(74) *Attorney, Agent, or Firm*—Oblon, Spivak, McClelland, Maier & Neustadt, P.C.

(57) ABSTRACT

A microorganism is provided which can metabolize a carbon source at a specific pH in a liquid medium containing L-glutamic acid at a saturation concentration and the carbon source, and which has ability to accumulate L-glutamic acid in an amount exceeding the amount corresponding to the saturation concentration in the liquid medium at the pH. Also provided is a method for producing L-glutamic acid by fermentation, which comprises culturing the microorganism in a liquid medium of which pH is adjusted to a pH at which L-glutamic acid is precipitated, to produce and accumulate L-glutamic acid and precipitate L-glutamic acid in the medium.

6 Claims, 8 Drawing Sheets

[88.0% / 935 aa]

```
  1' MQNSAMKPWLDSSWLAGANQSYIEQLYEDFLTDPDSVDAVWRSMFQQLPGTGVKPEQFHS
     xxxxx x xxxxx x xxxxx xxxxxxxxxxxxxxxx xxx xxxxxxxxxx xxxx
  1' MQNSALKAWLDSSYLSGANQSWIEQLYEDFLTDPDSVDANWRSTFQQLPGTGVKPDQFHS 61' ATREYFRRLAKDASRYTSSVTDPATNSKQVKVLQLINAFRFRGHQEANLDPLGLWKQDRV
     xxxxxxxxxxxxx x  xx xx xxxxxxxxx xxxxx xxxxxxxx xx x
 61' QTREYFRRLAKDASRYSSTISDPDTNVKQVKVLQLINAYRFRGHQHANLDPLGLWQQDKV 121' ADLDPAFHDLTDADFQESFNVGSFAIGKETMKLADLFDALKQTYCGSIGAEYMHINNTEE
     xxxxx xxxxx xxxxxx xxxxxx x  xxxxxxxx xxxxxxx  xx
121' ADLDPSFHDLTEADFQETFNVGSFASGKETMKLGELLEALKQTYCGPIGAEYMHITSTEE 181' KRWIQQRIESGASQTSFSGEEKKGFLKELTAAEGLEKYLGAKFPGAKRFSLEGGDALVPM
     xxxxxxxxx    x  xxxx xx xxxxxxxx xxxxxxxxxxxxxxxxxxxxx xx
181' KRWIQQRIESG--RATFNSEEKKRFLSELTAAEGLERYLGAKFPGAKRFSLEGGDALIPM 241' LREMIRHAGKSGTREVVLGMAHRGRLNVLINVLGKKPQDLFDEFSGKHKEHLGTGDVKYH
     x xxxxxx xxxxxxxxxxxxxxxxx xxxxxxxxxxxxxxxxx xxxxxxxxxxxxxx
239' LKEMIRHAGNSGTREVVLGMAHRGRLNVLVNVLGKKPQDLFDEFAGKHKEHLGTGDVKYH 301' MGFSSDIETEGGLVHLALAFNPSHLEIVSPVVMGSVRARLDRLAEPVSNKVLPITIHGDA
     xxxxx x xxxxxxxxxxxxxxxxxxxxxxx xxxxxxxxxx xx xxxxxxxxxxxxx
299' MGFSSDFQTDGGLVHLALAFNPSHLEIVSPVVIGSVRARLDRLDEPSSNKVLPITIHGDA 361' AVIGQGVVQETLNMSQARGYEVGGTVRIVINNQVGFTTSNPKDARSTPYCTDIGKMVLAP
     xx xxxxxxxxxxxxxx xxxxxxxxxxxxxxxxxxxxxx xxxxxxxxxxxxxxxx xx
359' AVTGQGVVQETLNMSKARGYEVGGTVRIVINNQVGFTTSNPLDARSTPYCTDIGKMVQAP 421  IFHVNADDPEAVAFVTRLALDYRNTFKRDVFIDLVCYRRHGHNEADEPSATQPLMYQKIK
     xxxxxxxxxxxxxxxxxxxx xxxxxxxxxxxxxx xxxxxxxxxxxxxxxxxxxxxxx
419' IFHVNADDPEAVAFVTRLALDFRNTFKRDVFIDLVSYRRHGHNEADEPSATQPLMYQKIK
```

*FIG. 2A*

```
481' KHPTPRKIYADRLEGEGVASQEDATEMVNLYRDALDAGECVVPEWRPMSLHSFTWSPYLN
     xxxxxxxxxx xx x xx xxxxxxxxxxxxxxx xxx xxxxx  xxxxxxxxxx
479' KHPTPRKIYADKLEQEKVATLEDATEMVNLYRDALDAGDCVVAEWRPMNMHSFTWSPYLN 541' HEWDEPYPAQVDMKRLKELALRISQVPEQIEVQSRVAKIYNDRKLMAEGEKAFDWGGAEN
     xxxxx xx x xxxx xxx xxx xxx x xxxxxxxx xx  xx xxx xxxxxxxx
539' HEWDEEYPNKVEMKRLQELAKRISTVPEAVEMQSRVAKIYGDRQAMAAGEKLFDWGGAEN 601' LAYATLVDEGIPVRLSGEDSGRGTFFHRHAVVHNQANGSTYTPLHHIHNSQGEFKVWDSV
     xxxxxxxxxxxxxxxxxxxxxxxxxxxxxxx xxx xxxxxxx xxxx xx x xxxxx
599' LAYATLVDEGIPVRLSGEDSGRGTFFHRHAVIHNQSNGSTYTPLQHIHNGQGAFRVWDSV 661' LSEEAVLAFEYGYATAEPRVLTIWEAQFGDFANGAQVVIDQFISSGEQKWGRMCGLVMLL
     xxxxxxxxxxxxxxxxxx xxxxxxxxxxxxxxxxxxxxxxxxxxxxxxxxxxxxxxxx
659' LSEEAVLAFEYGYATAEPRTLTIWEAQFGDFANGAQVVIDQFISSGEQKWGRMCGLVMLL 721' PHGYEGQGPEHSSARLERYLQLCAEQNMQVCVPSTPAQVYHMLRRQALRGMRRPLVVMSP
     xxxxxxxxxxxxxxxxxxxxxxxxxxxxxxxxxxxxxxxxxxxxxxxxxxxxxxxxxxx
719' PHGYEGQGPEHSSARLERYLQLCAEQNMQVCVPSTPAQVYHMLRRQALRGMRRPLVVMSP 781' KSLLRHPLAISSLDELANGSFQPAIGEIDDLDPQGVKRVVLCSGKVYYDLLEQRRKDEKT
     xxxxxxxx xxx xxxxx x xxxxxx xxx xxxxx xxxxxxxxxxxxxxxx
779' KSLLRHPLAVSSLEELANGTFLPAIGEIDELDPKGVKRVVMCSGKVYYDLLEQRRKNNQH 841' DVAIVRIEQLYPFPHQAVQEALKAYSHVQDFVWCQEEPLNQGAWYCSQHHFRDVVPFGAT
     xxxxxxxxxxxxxxx x xx x  xx xxxxxxxxxxxxxxxxxxxxxx x xxxx
839' DVAIVRIEQLYPFPHKAMQEVLQQFAHVKDFVWCQEEPLNQGAWYCSQHHFREVIPFGAS 901' LRYAGRPASASPAVGYMSVHQQQQQDLVNDALNVN
     xxxxxxxxxxxxxxxxxxxx xxxxxxxxxxx
899' LRYAGRPASASPAVGYMSVHQKQQQDLVNDALNVE
```

```
  1' MSSVDILVPDLPESVADATVATWHKKPGDAVSRDEVIVEIETDKVVLEVPASADGVLEAV
     ************************************ ****  ***************  * **
  1' MSSVDILPVDLPESVADATVATWHKKPGDAVVRDEVLVEIETDKVVLEVPASADGILDAV

61' LEDEGATVTSRQILGRLKEGNSAGKESSAKAESNDTTPAQRQTASLEEESSDALSPAIRR
     *****  *********** ******* ***  *      ****** *****    ********
 61' LEDEGTTVTSRQILGRLREGNSAGKETSAKSEEKASTPAQRQQASLEEQNNDALSPAIRR

121' LIAEHNLDAAQIKGTGVGGRLTREDVEKHLANKPQAEKAAAPAAGAATAQQPVANRSEKR
     * *******  ********************  *  *   ****  * **    *  *****
121' LLAEHNLDASAIKGTGVGGRLTREDVEKHLAKAPAKE--SAPAAAAPAAQPALAARSEKR

181' VPMTRLRKRVAERLLEAKNSTAMLTTFNEINMKPIMDLRKQYGDAFEKRHGVRLGFMSFY
     ************************************ **************  ************* ****** ********
179' VPMTRLRKRVAERLLEAKNSTAMLTTFNEVNMKPIMDLRKQYGEAFEKRHGIRLGFMSFY

241' IKAVVEALKRYPEVNASIDGEDVVYHNYFDVSIAVSTPRGLVTPVLRDVDALSMADIEKK
     ****************** ********* ************************ *   *******
239' VKAVVEALKRYPEVNASIDGDDVVYHNYFDVSMAVSTPRGLVTPVLRDVDTLGMADIEKK

301' IKELAVKGRDGKLTVDDLTGGNFTITNGGVFGSLMSTPIINPPQSAILGMHAIKDRPMAV
     ************* ***********************************************
299' IKELAVKGRDGKLTVEDLTGGNFTITNGGVFGSLMSTPIINPPQSAILGMHAIKDRPMAV

361' NGQVVILPMMYLALSYDHRLIDGRESVGYLVAVKEMLEDPARLLLDV
     ****  ******************** **  **  ****  ******
359' NGQVEILPMMYLALSYDHRLIDGRESVGFLVTIKELLEDPTRLLLDV
```

```
  1' MNLHEYQAKQLFARYGMPAPTGYACTTPREAEEAASKIGAG
     ****************   ********************
  1' MNLHEYQAKQLFARYGLPAPVGYACTTPREAEEAASKIGAGPWVVKCQVHAGGRGKAGGV
```

```
  1'                        AFSVFRCHSIMNCVSVCPKGLNPTRAIGHIKSMLLQRSA
                             ************************************** *
181' FLIDSRDTETDSRLDGLSDAFSVFRCHSIMNCVSVCPKGLNPTRAIGHIKSMLLQRNA
```

*FIG. 5*

METHOD FOR PRODUCING L-GLUTAMIC ACID BY FERMENTATION ACCOMPANIED BY PRECIPITATION

CROSS-REFERENCE TO RELATED APPLICATIONS

The present application is a continuation of U.S. Ser. No. 09/641,892, filed on Aug. 18, 2000 (now U.S. Pat. No. 7,015,010), which claims priority to Japanese application No. JP 11-234806, filed on Aug. 20, 1999, and to Japanese application No. JP 2000-78771, filed on Mar. 21, 2000.

BACKGROUND OF THE INVENTION

The present invention relates to a method for producing L-glutamic acid by fermentation accompanied by precipitation. L-Glutamic acid is widely used as a material for seasonings and so forth.

L-Glutamic acid is mainly produced by fermentative methods using so-called coryneformbacteria producing L-glutamic acid, which belong to the genus *Brevibacterium*, *Corynebacterium* or *Microbacterium*, or mutant strains thereof (Amino Acid Fermentation, pp. 195-215, Gakkai Shuppan Center, 1986). Methods for producing L-glutamic acid by fermentation using other bacterial strains are known and include a method using a microorganism belonging to the genus *Bacillus, Streptomyces, Penicillium* or the like (U.S. Pat. No. 3,220,929), a method using a microorganism belonging to the genus *Pseudomonas, Arthrobacter, Serratia, Candida* or the like (U.S. Pat. No. 3,563,857), a method using a microorganism belonging to the genus *Bacillus, Pseudomonas, Serratia, Aerobacter aerogenes* (currently referred to as *Enterobacter aerogenes*) or the like (Japanese Patent Publication (Kokoku) No. 32-9393), a method using a mutant strain of *Escherichia coli* (Japanese Patent Application Laid-open (Kokai) No. 5-244970) and so forth. In addition, the inventors of the present invention have proposed a method for producing L-glutamic acid by using a microorganism belonging to the genus *Klebsiella, Erwinia* or *Pantoea* (Japanese Patent Application Laid-open No. 2000-106869).

Further, there have been disclosed various techniques for improving L-glutamic acid-producing ability by enhancing activities of L-glutamic acid biosynthetic enzymes through the use of recombinant DNA techniques. For example, it has been reported that the introduction of a gene coding for citrate synthase derived from *Escherichia coli* or *Corynebacterium glutamicum* was effective for the enhancement of L-glutamic acid-producing ability in *Corynebacterium* or *Brevibacterium* bacteria (Japanese Patent Publication No. 7-121228). In addition, Japanese Patent Application Laid-open No. 61-268185 discloses a cell harboring recombinant DNA containing a glutamate dehydrogenase gene derived from *Corynebacterium* bacteria. Further, Japanese Patent Application Laid-open No. 63-214189 discloses a technique for improving L-glutamic acid-producing ability by amplifying a glutamate dehydrogenase gene, an isocitrate dehydrogenase gene, an aconitate hydratase gene and a citrate synthase gene.

Although L-glutamic acid productivity has been considerably increased by breeding of the aforementioned microorganisms or improvement of production methods, development of methods for more efficiently producing L-glutamic acid at a lower cost are still required to respond to the increasing future demand for L-glutamic acid.

A method wherein fermentation is performed with crystallizing L-amino acid accumulated in culture is known (Japanese Patent Application Laid-open No. 62-288). In this method, the L-amino acid concentration in the culture is maintained below a certain level by precipitating the accumulated L-amino acid in the culture. Specifically, L-tryptophan, L-tyrosine or L-leucine is precipitated during fermentation by adjusting the temperature and the pH of the culture or by adding a surface active agent to the medium.

While a fermentative method with precipitating L-amino acid is known as described above, amino acids suitable for this method are those of relatively low water solubility. No example exists for applying the method to highly water-soluble amino acids such as L-glutamic acid. In addition, the medium must have low pH to precipitate L-glutamic acid. However, L-glutamic acid-producing bacteria such as those mentioned above cannot grow under acidic conditions, and therefore L-glutamic acid fermentation is performed under neutral conditions (U.S. Pat. Nos. 3,220,929 and 3,032,474; Chao K. C. & Foster J. W., J. Bacteriol., 77, pp. 715–725 (1959)). Thus, production of L-glutamic acid by fermentation accompanied by precipitation is not known.

Furthermore, it is known that growth of most acidophile bacteria is inhibited by organic acids such as acetic acid, lactic acid and succinic acid (Yasuro Oshima Ed., "Extreme Environment Microorganism Handbook", p. 231, Science Forum; Borichewski R. M., J. Bacteriol., 93, pp. 597–599 (1967) etc.). Therefore, it is considered that many microorganisms are susceptible to L-glutamic acid, which is also an organic acid, under acidic conditions. There exists no report of microorganisms having L-glutamic acid-producing ability under acidic conditions has been attempted.

SUMMARY OF THE INVENTION

Based on the foregoing, an object of the present invention is to search and breed a microorganism that produces L-glutamic acid under low pH conditions and to provide a method for producing L-glutamic acid using an obtained microorganism by fermentation with precipitating L-glutamic acid.

The inventors of the present invention considered during the study for improvement of L-glutamic acid productivity by fermentation that inhibition of the production by L-glutamic acid accumulated in a medium at a high concentration was one of obstructions to the improvement of productivity. For example, cells have an excretory system and an uptake system for L-glutamic acid. However, if L-glutamic acid once excreted into the medium is incorporated into cells again, not only the production efficiency falls, but also the L-glutamic acid biosynthetic reactions are inhibited as a result. In order to avoid the inhibition of production by such accumulation of L-glutamic acid at high concentration, the inventors of the present invention screened microorganisms that can proliferate under acidic conditions and in the presence of a high concentration of L-glutamic acid. As a result, they successfully isolated microorganisms having such properties from a soil, and thus accomplished the present invention.

Thus, the present invention provides the following:

(1) A microorganism which can metabolize a carbon source at a specific pH in a liquid medium containing L-glutamic acid at a saturation concentration and the carbon source, and has ability to accumulate L-glutamic acid in an amount exceeding the amount corresponding to the saturation concentration in the liquid medium at the pH.

(2) The microorganism according to (1), which can grow in the liquid medium.

(3) The microorganism according to (1) or (2), wherein the pH is not more than 5.0.

(4) The microorganism according to any one of (1) to (3), which has at least one of the following characteristics:

(a) the microorganism is enhanced in activity of an enzyme that catalyzes a reaction for biosynthesis of L-glutamic acid; and (b) the microorganism is decreased in or deficient in activity of an enzyme that catalyzes a reaction branching from a biosynthetic pathway of L-glutamic acid and producing a compound other than L-glutamic acid.

(5) The microorganism according to (4), wherein the enzyme that catalyzes the reaction for biosynthesis of L-glutamic acid is at least one selected from citrate synthase, phosphoenolpyruvate carboxylase and glutamate dehydrogenase.

(6) The microorganism according to (4) or (5), wherein the enzyme that catalyzes the reaction branching from the biosynthetic pathway of L-glutamic acid and producing a compound other than L-glutamic acid is α-ketoglutarate dehydrogenase.

(7) The microorganism according to any one of (1) to (6), wherein the microorganism belongs to the genus *Enterobacter*.

(8) The microorganism according to (7), which is *Enterobacter agglomerans*.

(9) The microorganism according to (8), which has a mutation that causes less extracellular secretion of a viscous material compared with a wild strain when cultured in a medium containing a saccharide.

(10) A method for producing L-glutamic acid by fermentation, which comprises culturing a microorganism as defined in any one of (1) to (9) in a liquid medium of which pH is adjusted to a pH at which L-glutamic acid is precipitated, to produce and accumulate L-glutamic acid and precipitate L-glutamic acid in the medium.

(11) A method for screening a microorganism suitable for producing L-glutamic acid by fermentation with precipitating L-glutamic acid in a liquid medium, which comprises inoculating a sample containing microorganisms into an acidic medium containing L-glutamic acid at a saturation concentration and a carbon source, and selecting a strain that can metabolize the carbon source.

(12) The method according to (11), wherein a strain that can grow in the medium is selected as the strain that can metabolize the carbon source.

(13) The method according to (11) or (12), wherein a pH of the medium is not more than 5.0.

According to the method of the present invention, L-glutamic acid can be produced by fermentation with precipitating L-glutamic acid. As a result, L-glutamic acid in the medium is maintained below a certain concentration, and L-glutamic acid can be produced without suffering from the product inhibition by L-glutamic acid at a high concentration.

BRIEF EXPLANATION OF THE DRAWINGS

FIG. 2A and FIG. 2B show a comparison of the amino acid sequence deduced from the nucleotide sequence of the sucA gene derived from *Enterobacter agglomerans* and that derived from *Escherichia coli*. Upper sequence: *Enterobacter agglomerans* (SEQ ID NO: 3), lower sequence: *Escherichia coli* (SEQ ID NO: 8) (the same shall apply hereafter).

FIG. 3 shows comparison of the amino acid sequence deduced from the nucleotide sequence of the sucB gene derived from *Enterobacter agglomerans* (upper sequence—SEQ ID NO: 4) and that derived from *Escherichia coli* (lower sequence—SEQ ID NO: 9).

FIG. 4 shows comparison of the amino acid sequence deduced from the nucleotide sequence of the sucC gene derived from *Enterobacter agglomerans* (upper sequence—SEQ ID NO: 10) and that derived from *Escherichia coli* (lower sequence—SEQ ID NO: 11).

FIG. 5 shows comparison of the amino acid sequence deduced from the nucleotide sequence of the sdhB gene derived from *Enterobacter agglomerans* (upper sequence—SEQ ID NO: 2) and that derived from *Escherichia coli* (lower sequence—SEQ ID NO: 12).

DETAILED DESCRIPTION OF THE INVENTION

Figure 1:
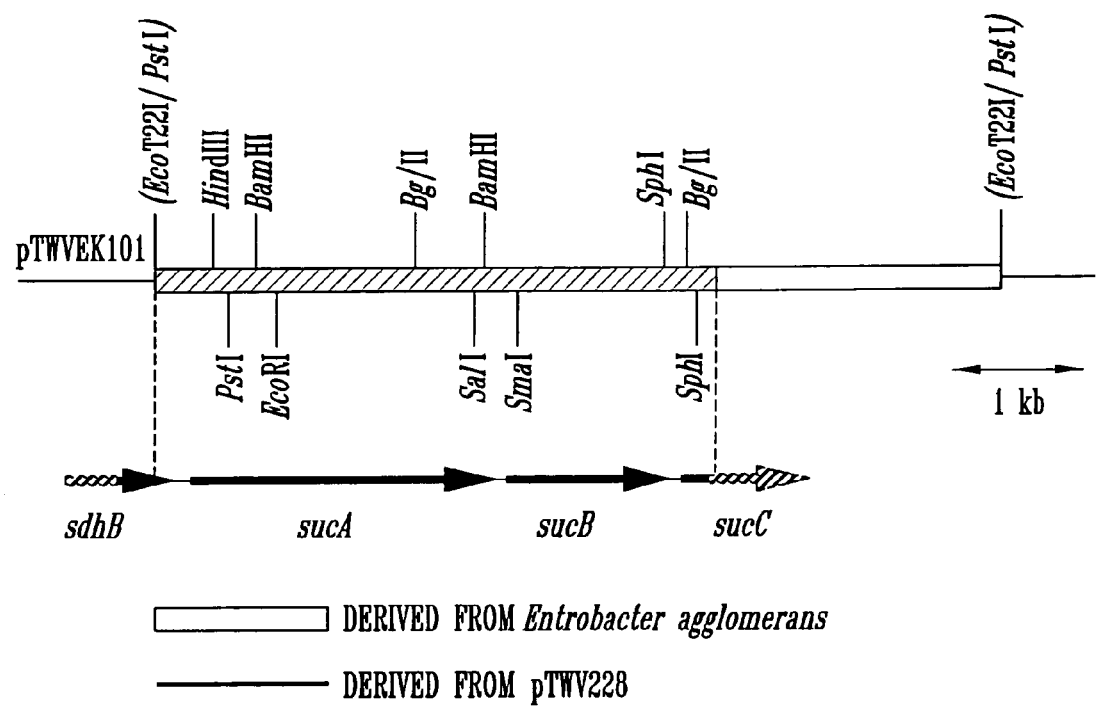
FIG. 1 shows a restriction map of a DNA fragment derived from *Enterobacter agglomerans* pTWVEK101.

Hereafter, the present invention will be explained in detail.

The microorganism of the present invention is a microorganism that (1) can metabolize a carbon source at a specific pH in a liquid medium containing L-glutamic acid at a saturation concentration and the carbon source and (2) has ability to accumulate L-glutamic acid in an amount exceeding the amount corresponding to the saturation concentration in the liquid medium at the pH.

The term "saturation concentration" means a concentration of L-glutamic acid dissolved in a liquid medium when the liquid medium is saturated with L-glutamic acid.

Hereafter, a method for screening a microorganism that can metabolize a carbon source in a liquid medium containing L-glutamic acid at a saturation concentration and the carbon source at a specific pH will be described. A sample containing microorganisms is inoculated into a liquid medium containing L-glutamic acid at a saturation concentration and a carbon source at a specific pH, and a strain that can metabolize the carbon source is selected. The specific pH is not particularly limited, but is usually not more than about 5.0, preferably not more than about 4.5, more preferably not more than about 4.3. The microorganism of the present invention is used to produce L-glutamic acid by fermentation with precipitating L-glutamic acid. If the pH is too high, it becomes difficult to allow the microorganism to produce L-glutamic acid enough for precipitation. Therefore, pH is preferably in the aforementioned range.

If pH of an aqueous solution containing L-glutamic acid is lowered, the solubility of L-glutamic acid significantly falls around pKa of γ-carboxyl group (4.25, 25° C.). The solubility becomes the lowest at the isoelectric point (pH 3.2) and L-glutamic acid exceeding the amount corresponding to the saturation concentration is precipitated. While it depends on the medium composition, L-glutamic acid is usually dissolved in an amount of 10 to 20 g/L at pH 3.2, 30 to 40 g/L at pH 4.0 and 50 to 60 g/L at pH 4.7, at about 30° C. Usually pH does not need to be made below 3.0, because the L-glutamic acid precipitating effect plateaus when pH goes below a certain value. However, pH may be below 3.0.

In addition, the expression that a microorganism "can metabolize the carbon source" means that it can proliferate or can consume the carbon source even though it cannot proliferate. Therefore, this phrase indicates that the microorganism catabolizes carbon sources such as saccharides or organic acids. Specifically, for example, if a microorganism proliferates when cultured in a liquid medium containing L-glutamic acid at a saturation concentration at pH 5.0 to 4.0, preferably pH 4.5 to 4.0, more preferably pH 4.3 to 4.0, still more preferably pH 4.0 at an appropriate temperature, for example, 28° C., 37° C. or 50° C. for 2 to 4 days, this microorganism can metabolize the carbon source in the medium.

Further, for example, even if a microorganism does not proliferate when it is cultured in a liquid medium containing L-glutamic acid at a saturation concentration at pH 5.0 to 4.0, preferably pH 4.5 to 4.0, more preferably pH 4.3 to 4.0, still more preferably pH 4.0 at an appropriate temperature, for example, 28° C., 37° C. or 50° C. for 2 to 4 days, the microorganism which consumes the carbon source in the medium is that can metabolize the carbon source in the medium.

The microorganism which can metabolize the carbon source includes a microorganism which can grow in the liquid medium.

The expression that a microorganism "can grow" means that it can proliferate or can produce L-glutamic acid even though it cannot proliferate. Specifically, for example, if a microorganism proliferates when cultured in a liquid medium containing L-glutamic acid at a saturation concentration at pH 5.0 to 4.0, preferably pH 4.5 to 4.0, more preferably pH 4.3 to 4.0, still more preferably pH 4.0 at an appropriate temperature, for example, 28° C., 37° C. or 50° C. for 2 to 4 days, this microorganism can grow in the medium.

Further, for example, even if a microorganism does not proliferate when it is cultured in a liquid synthetic medium containing L-glutamic acid at a saturation concentration at pH 5.0 to 4.0, preferably pH 4.5 to 4.0, more preferably pH 4.3 to 4.0, still more preferably pH 4.0 at an appropriate temperature, for example, 28° C., 37° C. or 50° C. for 2 to 4 days, the microorganism which increases the amount of L-glutamic acid in the medium is that can grow in the medium.

The selection described above may be repeated two or more times under the same conditions or with changing pH or the concentration of L-glutamic acid. An initial selection can be performed in a medium containing L-glutamic acid at a concentration lower than the saturation concentration, and thereafter a subsequent selection can be performed in a medium containing L-glutamic acid at a saturation concentration. Further, strains with favorable properties such as superior proliferation rate may be selected.

In addition to the property described above, the microorganism of the present invention has an ability to accumulate L-glutamic acid in an amount exceeding the amount corresponding to the saturation concentration of L-glutamic acid in a liquid medium. The pH of the aforementioned liquid medium is preferably the same as or close to that of the medium used for screening a microorganism having the aforementioned property (1). Usually, a microorganism becomes susceptible to L-glutamic acid at a high concentration as pH becomes lower. Therefore, it is preferred that pH is not low from the viewpoint of resistance to L-glutamic acid, but low pH is preferred from the viewpoint of production of L-glutamic acid with precipitating it. To satisfy these conditions, pH may be in the range of 3 to 5, preferably 4 to 5, more preferably 4.0 to 4.7, still more preferably 4.0 to 4.5, particularly preferably 4.0 to 4.3.

As the microorganism of the present invention or breeding materials therefor, there can be mentioned, for example, microorganisms belonging to the genus *Enterobacter, Klebsiella, Serratia, Pantoea, Erwinia, Escherichia, Corynebacterium, Alicyclobacillus, Bacillus, Saccharomyces* or the like. Among these, microorganisms belonging to the genus *Enterobacter* are preferred. Hereafter, the microorganism of the present invention will be explained mainly for microorganisms belonging to the genus *Enterobacter*, but the present invention can be applied to microorganism belonging to other genera and not limited to the genus *Enterobacter*.

As microorganisms belonging to the *Enterobacter*, there can be specifically mentioned *Enterobacter agglomerans*, preferably the *Enterobacter agglomerans* AJ13355 strain. This strain was isolated from a soil in Iwata-shi, Shizuoka, Japan as a strain that can proliferate in a medium containing L-glutamic acid and a carbon source at low pH.

The physiological properties of AJ13355 are as follows:
(1) Gram staining: negative
(2) Behavior against oxygen: facultative anaerobic
(3) Catalase: positive
(4) Oxidase: negative
(5) Nitrate-reducing ability: negative
(6) Voges-Proskauer test: positive
(7) Methyl Red test: negative
(8) Urease: negative
(9) Indole production: positive
(10) Motility: motile
(11) $H_2S$ production in TSI medium: weakly active
(12) β-galactosidase: positive
(13) Saccharide-assimilating property:
Arabinose: positive
Sucrose: positive
Lactose: positive
Xylose: positive
Sorbitol: positive
Inositol: positive
Trehalose: positive
Maltose: positive
Glucose: positive
Adonitol: negative
Raffinose: positive
Salicin: negative
Melibiose: positive
(14) Glycerol-assimilating property: positive
(15) Organic acid-assimilating property:
Citric acid: positive
Tartaric acid: negative
Gluconic acid: positive Acetic acid: positive Malonic acid: negative

(16) Arginine dehydratase: negative

(17) Ornithine decarboxylase: negative

(18) Lysine decarboxylase: negative

(19) Phenylalanine deaminase: negative

(20) Pigment formation: yellow

(21) Gelatin liquefaction ability: positive

(22) Growth pH: growth is possible at pH 4.0, good growth at pH 4.5 to 7

(23) Growth temperature: good growth at 25° C., good growth at 30° C., good growth at 37° C., growth is possible at 42° C., growth is not possible at 45° C.

Based on these bacteriological properties, AJ13355 was determined as *Enterobacter agglomerans*.

The *Enterobacter agglomerans* AJ13355 was deposited at the National Institute of Bioscience and Human-Technology, Agency of Industrial Science and Technology, Ministry of International Trade and Industry (postal code: 305–8566, 1-3, Higashi 1-chome, Tsukuba-shi, Ibaraki, Japan) on Feb. 19, 1998 and received an accession number of FERM P-16644. It was then transferred to an international deposition under the provisions of Budapest Treaty on Jan. 11, 1999 and received an accession number of FERM BP-6614.

The microorganism of the present invention may be a microorganism originally having L-glutamic acid-producing ability or one having L-glutamic acid-producing ability imparted or enhanced by breeding through use of mutation treatment, recombinant DNA techniques or the like.

L-Glutamic acid-producing ability can be imparted or enhanced by, for example, increasing activity of an enzyme that catalyzes a reaction for biosynthesis of L-glutamic acid. L-Glutamic acid-producing ability can also be enhanced by decreasing activity of an enzyme that catalyzes a reaction branching from the biosynthetic pathway of L-glutamic acid and producing a compound other than L-glutamic acid, or making the activity deficient.

Enzymes that catalyze are action for biosynthesis of L-glutamic acid, include: glutamate dehydrogenase (hereafter, also referred to as "GDH"), glutamine synthetase, glutamate synthase, isocitrate dehydrogenase, aconitate hydratase, citrate synthase (hereafter, also referred to as "CS"), phosphoenolpyruvate carboxylase (hereafter, also referred to as "PEPC"), pyruvate dehydrogenase, pyruvate kinase, enolase, phosphoglyceromutase, phosphoglycerate kinase, glyceraldehyde-3-phosphate dehydrogenase, triosephosphate isomerase, fructose bisphosphate aldolase, phosphofructokinase, glucose phosphate isomerase and so forth. Among these enzymes, one, two or three of CS, PEPC and GDH are preferred. Further, it is preferred that the activities of all the three enzymes, CS, PEPC and GDH, are enhanced in the microorganism of the present invention. In particular, CS of *Brevibacterium lactofermentum* is preferred, because it does not suffer from inhibition by α-ketoglutaric acid, L-glutamic acid and NADH.

In order to enhance the activity of CS, PEPC or GDH, for example, a gene coding for CS, PEPC or GDH may be cloned on an appropriate plasmid and a host microorganism may be transformed with the obtained plasmid. The copy number of the gene coding for CS, PEPC or GDH (hereafter, abbreviated as "gltA gene", "ppc gene" and "gdhA gene", respectively) in the transformed strain cell increases, resulting in the increase of the activity of CS, PEPC or GDH.

The cloned gltA gene, ppc gene and gdhA gene are introduced into the aforementioned starting parent strain solely or in combination of arbitrary two or three kinds of them. When two or three kinds of the genes are introduced, two or three kinds of the genes may be cloned on one kind of plasmid and introduced into the host, or separately cloned on two or three kinds of plasmids that can coexist and introduced into the host.

Two or more kinds of genes coding for enzymes of the same kind, but derived from different microorganisms may be introduced into the same host.

The plasmids described above are not particularly limited so long as they are autonomously replicable in cells of a microorganism belonging to, for example, the genus *Enterobacter* or the like, but, for example, there can be mentioned pUC19, pUC18, pBR322, pHSG299, pHSG298, pHSG399, pHSG398, RSF1010, pMW119, pMW118, pMW219, pMW218, pACYC177, pACYC184 and so forth. Besides these, vectors of phage DNA can also be used.

Transformation can be performed by, for example, the method of D. M. Morrison (Methods in Enzymology, 68, 326 (1979)), the method wherein permeability of DNA is increased by treating recipient bacterium cells with calcium chloride (Mandel M. and Higa A., J. Mol. Biol., 53, 159 (1970)), the electroporation (Miller J. H., "A Short Course in Bacterial Genetics", Cold Spring Harbor Laboratory Press, U.S.A. 1992) or the like.

The activity of CS, PEPC or GDH can also be increased by allowing multiple copies of a gltA gene, a ppc gene or a gdhA gene to be present on chromosomal DNA of the aforementioned starting parent strain to be a host. In order to introduce multiple copies of the gltA gene, the ppc gene or the gdhA gene on chromosomal DNA of a microorganism belonging to the genus *Enterobacter* or the like, a sequence of which multiple copies are present on the chromosomal DNA, such as repetitive DNA and inverted repeats present at termini of a transposable element, can be used. Alternatively, multiple copies of the genes can be introduced on to chromosomal DNA by utilizing transfer of a transposon containing the gltA gene, the ppc gene or the gdhA gene. As a result, the copy number of the gltA gene, the ppc gene or the gdhA gene in a transformed strain cell is increased, and thus the activity of CS, PEPC or GDH is increased.

As organisms to be a source of the gltA gene, the ppc gene or the gdhA gene of which copy number is increased, any organism can be used so long as it has activity of CS, PEPC or GDH. Inter alia, bacteria, which are prokaryotes, for example, those belonging to the genus *Enterobacter, Klebsiella, Erwinia, Pantoea, Serratia, Escherichia, Corynebacterium, Brevibacterium* and *Bacillus* are preferred. As specific examples, there can be mentioned *Escherichia coli, Brevibacterium lactofermentum* and so forth. The gltA gene, the ppc gene and the gdhA gene can be obtained from chromosomal DNA of the microorganisms described above.

The gltA gene, the ppc gene and the gdhA gene can be obtained by using a mutant strain which is deficient in the activity of CS, PEPC or GDH to isolate a DNA fragment which complements the auxotrophy from chromosomal DNA of the aforementioned microorganisms. Since the nucleotide sequences of these genes of *Escherichia* and *Corynebacterium* bacteria have already been elucidated (Biochemistry, 22, pp. 5243–5249 (1983); J. Biochem., 95, pp. 909–916 (1984); Gene, 27, pp. 193–199 (1984); Microbiology, 140, pp. 1817–1828 (1994); Mol. Gen. Genet., 218, pp. 330–339 (1989); Molecular Microbiology, 6, pp. 317–326 (1992)), they can also be obtained by PCR utilizing primers synthesized based on each nucleotide sequence and chromosomal DNA as a template.

The activity of CS, PEPC or GDH can also be increased by enhancing the expression of the gltA gene, the ppc gene or the gdhA gene besides the aforementioned amplification of the genes. For example, the expression can be enhanced by replacing a promoter for the gltA gene, the ppc gene or the gdhA gene with other stronger promoters. For example, strong promoters are known to include: lac promoter, trp promoter, trc promoter, tac promoter, $P_R$ promoter and $P_L$ promoter of the lamda phage and so forth. The gltA gene, the ppc gene and the gdhA gene of which promoter is replaced are cloned on a plasmid and introduced into the host microorganism, or introduced onto the chromosomal DNA of the host microorganism by using repetitive DNA, inverted repeats, transposon or the like.

The activity of CS, PEPC or GDH can also be enhanced by replacing the promoter of the gltA gene, the ppc gene or the gdhA gene on the chromosome with other stronger promoters (see WO 87/03006 and Japanese Patent Application Laid-open No. 61-268183), or inserting a strong promoter in the upstream of the coding sequence of each gene (see Gene, 29, pp. 231–241 (1984)). Specifically, homologous recombination can be performed between DNA containing the gltA gene, the ppc gene or the gdhA gene of which promoter is replaced with a stronger one or a part thereof and the corresponding gene on the chromosome.

Examples of the enzyme which catalyze a reaction branching from the biosynthetic pathway of the L-glutamic acid and producing a compound other than L-glutamic acid include α-ketoglutarate dehydrogenase (hereafter, also referred to as "αKGDH"), isocitrate lyase, phosphate acetyltransferase, acetate kinase, acetohydroxy acid synthase, acetolactate synthase, formate acetyltransferase, lactate dehydrogenase, glutamate decarboxylase, 1-pyrroline dehydrogenase and so forth. Among these enzymes, αKGDH is preferred.

In order to obtain a decrease or deficiency of the activity of the aforementioned enzyme in a microorganism belonging to the genus *Enterobacter* or the like, mutation causing decrease or deficiency of the intracellular activity of the enzyme can be introduced into the gene of the aforementioned enzyme by a usual mutagenesis or genetic engineering method.

Examples of the mutagenesis method include, for example, methods utilizing irradiation with X-ray or ultraviolet ray, methods utilizing treatment with a mutagenic agent such as N-methyl-N'-nitro-N-nitrosoguanidine, and so forth. The site where the mutation is introduced to the gene may be in a coding region coding for an enzyme protein, or a region for regulating expression such as a promoter.

Examples of the genetic engineering methods include, for example, methods utilizing gene recombination, transduction, cell fusion and so forth. For example, a drug resistance gene is inserted into a cloned target gene to prepare a gene that has lost its function (defective gene). Subsequently, this defective gene is introduced into a cell of a host microorganism, and the target gene on the chromosome is replaced with the aforementioned defective gene by utilizing homologous recombination (gene disruption).

A decrease or deficiency of intracellular activity of the target enzyme and the degree of decrease of the activity can be determined by measuring the enzyme activity of a cell extract or a purified fraction thereof obtained from a candidate strain and comparing with that of a wild strain. For example, the αKGDH activity can be measured by the method of Reed et al. (Reed L. J. and Mukherjee B. B., Methods in Enzymology, 13, pp. 55–61 (1969)).

Depending on the target enzyme, the target mutant strain can be selected based on the phenotype of the mutant strain. For example, a mutant strain which is deficient in the αKGDH activity or decreases in the αKGDH activity cannot proliferate or shows a markedly reduced proliferation rate in a minimal medium containing glucose or a minimal medium containing acetic acid or L-glutamic acid as an exclusive carbon source under aerobic conditions. However, normal proliferation is enabled even under the same condition by adding succinic acid or lysine, methionine and diaminopimelic acid to a minimal medium containing glucose. By utilizing these phenomena as indicators, mutant strains with decreased αKGDH activity or deficient in the activity can be selected.

A method for preparing the αKGDH gene deficient strain of *Brevibacterium lactofermentum* by utilizing homologous recombination is described in detail in WO 95/34672. Similar methods can be applied to the other microorganisms.

Further, techniques such as cloning of genes and cleavage and ligation of DNA, transformation and so forth are described in detail in Molecular Cloning, 2nd Edition, Cold Spring Harbor Press, 1989 and so forth.

As a specific example of a mutant strain deficient in αKGDH activity or with decreased αKGDH activity obtained as described above, there can be mentioned *Enterobacter agglomerans* AJ13356. *Enterobacter agglomerans* AJ13356 was deposited at the National Institute of Bioscience and Human-Technology, Agency of Industrial Science and Technology, Ministry of International Trade and Industry (postal code: 305-8566, 1-3, Higashi 1-chome, Tsukuba-shi, Ibaraki, Japan) on Feb. 19, 1998 and received an accession number of FERM P-16645. It was then transferred to an international deposition under the provisions of Budapest Treaty on Jan. 11, 1999 and received an accession number of FERM BP-6615. The *Enterobacter agglomerans* AJ13356 is deficient in αKGDH activity as a result of disruption of the αKGDH-E1 subunit gene (sucA).

When *Enterobacter agglomerans*, an example of the microorganism used in the present invention, is cultured in a medium containing a saccharide, a viscous material is extracellularly secreted, resulting in low operation efficiency. Therefore, when *Enterobacter agglomerans* having such a property of secreting the viscous material is used, it is preferable to use a mutant strain that secretes less the viscous material compared with a wild strain. Examples of mutagenesis methods include, for example, methods utilizing irradiation with X ray or ultraviolet ray, method utilizing treatment with a mutagenic agent such as N-methyl-N'-nitro-N-nitrosoguanidine and so forth. A mutant strain with decreased secretion of the viscous material can be selected by inoculating mutagenized bacterial cells in a medium containing a saccharide, for example, LB medium plate containing 5 g/L of glucose, culturing them with tilting the plate about 45 degrees and selecting a colony which does not show flowing down of liquid.

In the present invention, impartation or enhancement of L-glutamic acid-producing ability and impartation of other favorable properties such as mutation for less viscous material secretion described above can be carried out in an arbitrary order.

By culturing the microorganism of the present invention in a liquid medium of which pH is adjusted to a pH at which L-glutamic acid is precipitated, L-glutamic acid can be produced and accumulated with precipitating it in the medium. L-Glutamic acid can also be precipitated by starting the culture at a neutral pH and then ending it at a pH at which L-glutamic acid is precipitated.

The pH at which L-glutamic acid is precipitated means one at which L-glutamic acid is precipitated when the microorganism produces and accumulates L-glutamic acid.

As the aforementioned medium, a usual nutrient medium containing a carbon source, a nitrogen source, mineral salts and organic trace nutrients such as amino acids and vitamins as required can be used so long as pH is adjusted to a pH at which L-glutamic acid is precipitated. Either a synthetic medium or a natural medium can be used. The carbon source and the nitrogen source used in the medium can be any ones so long as they can be used by the cultured strain.

As the carbon source, saccharides such as glucose, glycerol, fructose, sucrose, maltose, mannose, galactose, starch hydrolysate and molasses are used. In addition, organic acids such as acetic acid and citric acid may be used each alone or in combination with another carbon source.

As the nitrogen source, ammonia, ammonium salts such as ammonium sulfate, ammonium carbonate, ammonium chloride, ammonium phosphate and ammonium acetate, nitrates and so forth are used.

As the organic trace nutrients, amino acids, vitamins, fatty acids, nucleic acids, those containing these substances such as peptone, casamino acid, yeast extract and soybean protein decomposition products are used. When an auxotrophic mutant strain that requires an amino acid and so forth for metabolization or growth is used, the required nutrient must be supplemented.

As mineral salts, phosphates, magnesium salts, calcium salts, iron salts, manganese salts and so forth are used.

As for the culture method, aeration culture is usually performed with controlling the fermentation temperature to be 20 to 42° C. and pH to be 3 to 5, preferably 4 to 5, more preferably 4 to 4.7, particularly preferably 4 to 4.5. Thus, after about 10 hours to 4 days of culture, a substantial amount of L-glutamic acid is accumulated in the culture. Accumulated L-glutamic acid exceeding the amount corresponding to the saturation concentration is precipitated in the medium.

After completion of the culture, L-glutamic acid precipitated in the culture can be collected by centrifugation, filtration or the like. L-Glutamic acid dissolved in the medium can be collected according to known methods. For example, the L-glutamic acid can be isolated by concentrating the culture broth to crystallize it or isolated by ion exchange chromatography or the like. L-Glutamic acid precipitated in the culture broth may be isolated together with L-glutamic acid that have been dissolved in the medium after it is crystallized.

According to the method of the present invention, L-glutamic acid exceeding the amount corresponding to the saturation concentration is precipitated, and the concentration of L-glutamic acid dissolved in the medium is maintained at a constant level. Therefore, influence of L-glutamic acid at a high concentration on microorganisms can be reduced. Accordingly, it becomes possible to breed a microorganism having further improved L-glutamic acid-producing ability. Further, since L-glutamic acid is precipitated as crystals, acidification of the culture broth by accumulation of L-glutamic acid is suppressed, and therefore the amount of alkali used for maintaining pH of the culture can significantly be reduced.

EXAMPLES

Hereafter, the present invention will be more specifically explained with reference to the following examples.

<1> Screening of Microorganism Having L-Glutamic Acid Resistance in Acidic Environment Screening of a microorganism having L-glutamic acid resistance in an acidic environment was performed as follows. Each of about 500 samples obtained from nature including soil, fruits, plant bodies, river water in an amount of 1 g was suspended in 5 mL of sterilized water, of which 200 µL was coated on 20 mL of solid medium of which pH was adjusted to 4.0 with HCl. The composition of the medium was as follows: 3 g/L of glucose, 1 g/L of $(NH_4)_2SO_4$, 0.2 g/L of $MgSO_4.7H_2O$, 0.5 g/L of $KH_2PO_4$, 0.2 g/L of NaCl, 0.1 g/L of $CaCl_2.7H_2O$, 0.01 g/L of $FeSO_4.7H_2O$, 0.01 g/L of $MnSO_4.4H_2O$, 0.72 mg/L of $ZnSO_4.2H_2O$, 0.64 mg/L of $CuSO_4.5H_2O$, 0.72 mg/L of $CoCl_2.6H_2O$, 0.4 mg/L of boric acid, 1.2 mg/L of $Na_2MoO_4.2H_2O$, 50 µg/L of biotin, 50 µg/L of calcium pantothenate, 50 µg/L of folic acid, 50 µg/L of inositol, 50 µg/L of niacin, 50 µg/L of p-aminobenzoic acid, 50 µg/L of pyridoxine hydrochloride, 50 µg/L of riboflavin, 50 µg/L of thiamine hydrochloride, 50 mg/L of cycloheximide, 20 g/L of agar.

The media plated on which the above samples were plated were incubated at 28° C., 37° C. or 50° C. for 2 to 4 days and 378 strains each forming a colony were obtained.

Subsequently, each of the strains obtained as described above was inoculated in a test tube of 16.5 cm in length and 14 mm in diameter containing 3 mL of liquid medium (adjusted to pH 4.0 with HCl) containing a saturation concentration of L-glutamic acid and cultured at 28° C., 37° C. or 50° C. for 24 hours to 3 days with shaking. Then, the grown strains were selected. The composition of the aforementioned medium was follows: 40 g/L of glucose, 20 g/L of $(NH_4)_2SO_4$, 0.5 g/L of $MgSO_4.7H_2O$, 2 g/L of $KH_2PO_4$, 0.5 g/L of NaCl, 0.25 g/L of $CaCl_2.7H_2O$, 0.02 g/L of $FeSO_4.7H_2O$, 0.02 g/L of $MnSO_4.4H_2O$, 0.72 mg/L of $ZnSO_4.2H_2O$, 0.64 mg/L of $CuSO_4.5H_2O$, 0.72 mg/L of $CoCl_2.6H_2O$, 0.4 mg/L of boric acid, 1.2 mg/L of $Na_2MoO_4.2H_2O$, 2 g/L of yeast extract.

Thus, 78 strains of microorganisms having L-glutamic acid resistance in an acidic environment were successfully obtained.

<2> Selection of Strains with Superior Growth Rate in Acidic Environment from Microorganisms Having L-glutamic Acid Resistance The various microorganisms having L-glutamic acid resistance in an acidic environment obtained as described above were each inoculated into a test tube of 16.5 cm in length and 14 mm in diameter containing 3 mL of medium (adjusted to pH 4.0 with HCl) obtained by adding 20 g/L of glutamic acid and 2 g/L of glucose to M9 medium (Sambrook, J., Fritsh, E. F. and Maniatis, T., "Molecular Cloning", Cold Spring Harbor Laboratory Press, 1989), and the turbidity of the medium was measured in the time course to select strains with a favorable growth rate. As a result, as a strain showing favorable growth, the AJ13355 strain was obtained from a soil in Iwata-shi, Shizuoka, Japan. This strain was determined as *Enterobacter agglomerans* based on its bacteriological properties described above.

<3> Acquisition of Strain with Less Viscous Material Secretion from *Enterobacter agglomerans* AJ13355 Strain Since the *Enterobacter agglomerans* AJ13355 strain extracellularly secretes a viscous material when cultured in a medium containing a saccharide, operation efficiency is not favorable. Therefore, a strain with less viscous material secretion was obtained by the ultraviolet irradiation method (Miller, J. H. et al., "A Short Course in Bacterial Genetics; Laboratory Manual", p. 150, Cold Spring Harbor Laboratory Press, 1992).

The *Enterobacter agglomerans* AJ13355 strain was irradiated with ultraviolet ray for 2 minutes at the position 60 cm away from a 60-W ultraviolet lamp and cultured in LB medium overnight to fix mutation. The mutagenized strain was diluted and inoculated in LB medium containing 5 g/L of glucose and 20 g/L of agar so that about 100 colonies per plate would emerge and cultured at 30° C. overnight with tilting the plate about 45 degrees, and then 20 colonies showing no flowing down of the viscous material were selected.

As a strain satisfying conditions that no revertant emerged even after 5 times of subculture in LB medium containing 5 g/L of glucose and 20 g/L of agar, and that there should be observed growth equivalent to the parent strain in LB medium, LB medium containing 5 g/L of glucose and M9 medium (Sambrook, J. et al., Molecular Cloning, 2nd Edition, Cold Spring Harbor Press, 1989) to which 20 g/L of L-glutamic acid and 2 g/L of glucose were added and of which pH was adjusted to 4.5 with HCl, SC17 strain was selected from the strains selected above.

<4> Construction of Glutamic Acid-Producing Bacterium from *Enterobacter agglomerans* SC17 Strain (1) Preparation of αKGDH Deficient Strain from *Enterobacter agglomerans* SC17 Strain A strain deficient in αKGDH and with enhanced L-glutamic acid biosynthetic system was prepared from the *Enterobacter agglomerans* SC17 strain.

(i) Cloning of αKGDH Gene (Hereafter, Referred to as "sucAB") of *Enterobacter agglomerans* AJ13355 Strain The sucAB gene of the *Enterobacter agglomerans* AJ13355 strain was cloned by selecting a DNA fragment complementing the acetic acid-unassimilating property of the αKGDH-E1 subunit gene (hereafter, referred to as "sucA") deficient strain of *Escherichia coli* from chromosomal DNA of the *Enterobacter agglomerans* AJ13355 strain.

The chromosomal DNA of the *Enterobacter agglomerans* AJ13355 strain was isolated by a method usually employed when chromosomal DNA is extracted from *Escherichia coli* (Text for Bioengineering Experiments, Edited by the Society for Bioscience and Bioengineering, Japan, pp. 97–98, Baifukan, 1992). The pTWV228 (resistant to ampicillin) used as a vector was commercially available one from Takara Shuzo Co., Ltd.

The chromosomal DNA of the AJ13355 strain digested with EcoT221 and pTWV228 digested with PstI were ligated by using T4 ligase and used to transform the sucA deficient *Escherichia coli* JRG465 strain (Herbert, J. et al., Mol. Gen. Genetics, 105, 182 (1969)). A strain growing in an acetate minimal medium was selected from the transformant strains obtained above, and a plasmid was extracted from it and designated as pTWVEK101. The *Escherichia coli* JRG465 strain harboring pTWVEK101 recovered auxotrophy for succinic acid or L-lysine and L-methionine besides the acetic acid-assimilating property. This suggests that pTWVEK101 contains the sucA gene of *Enterobacter agglomerans*.

FIG. 1 shows the restriction map of a DNA fragment derived from *Enterobacter agglomerans* in pTWVEK101. The determined nucleotide sequence of the hatched portion in FIG. 1 is shown as SEQ ID NO: 1. In this sequence, nucleotide sequences considered to be two full length ORFs and two nucleotide sequences considered to be partial sequences of the ORFs were found. SEQ ID NOS: 2 to 5 show amino acid sequences that can be encoded by these ORFs or partial sequences in an order from the 5' end. As a result of homology search for these, it was revealed that the portion of which nucleotide sequences were determined contained a 3'-end partial sequence of the succinate dehydrogenase iron-sulfur protein gene (sdhB), full length sucA and αKGDH-E2 subunit gene (sucB), and 5'-end partial sequence of the succinyl CoA synthetase β subunit gene (sucC). The results of comparison of the amino acid sequences deduced from these nucleotide sequences with those derived from *Escherichia coli* (Eur. J. Biochem., 141, pp. 351–359 (1984); Eur. J. Biochem., 141, pp. 361–374 (1984); Biochemistry, 24, pp. 6245–6252 (1985)) are shown in FIGS. 2 to 5. Thus, the amino acid sequences each showed very high homology. In addition, it was found that a cluster of sdhB-sucA-sucB-sucC was constituted on the chromosome of *Enterobacter agglomerans* as in *Escherichia coli* (Eur. J. Biochem., 141, pp. 351–359 (1984); Eur. J. Biochem., 141, pp. 361–374 (1984); Biochemistry, 24, pp. 6245–6252 (1985)).

(ii) Acquisition of αKGDH Deficient Strain Derived from *Enterobacter agglomerans* SC17 Strain The homologous recombination was performed by using the sucAB gene of *Enterobacter agglomerans* obtained as described above to obtain an αKGDH deficient strain of *Enterobacter agglomerans*.

After pTWVEK101 was digested with SphI to excise a fragment containing sucA, the fragment was blunt-ended with Klenow fragment (Takara Shuzo Co., Ltd.) and ligated with pBR322 digested with EcoRI and blunt-ended with Klenow fragment, by using T4 DNA ligase (Takara Shuzo Co., Ltd.). The obtained plasmid was digested at the restriction enzyme BglII recognition site positioned substantially at the center of sucA by using this enzyme, blunt-ended with Klenow fragment, and then ligated again by using T4 DNA ligase. It was considered that the sucA gene did not function because a frame shift mutation was introduced into sucA of the plasmid newly constructed through the above procedure.

The plasmid constructed as described above was digested with a restriction enzyme ApaLI, and subjected to agarose gel electrophoresis to recover a DNA fragment containing sucA into which the frame shift mutation was introduced and a tetracycline resistance gene derived from pBR322. The recovered DNA fragment was ligated again by using T4 DNA ligase to construct a plasmid for disrupting the αKGDH gene.

The plasmid for disrupting the αKGDH gene obtained as described above was used to transform the *Enterobacter agglomerans* SC17 strain by electroporation (Miller, J. H., "A Short Course in Bacterial Genetics; Handbook", p. 279, Cold Spring Harbor Laboratory Press, U.S.A., 1992), and a strain where in sucA on the chromosome was replaced with a mutant type one by homologous recombination of the plasmid was obtained by using the tetracycline resistance as an indicator. The obtained strain was designated as SC17sucA strain.

In order to confirm that the SC17sucA strain was deficient in the αKGDH activity, the enzyme activity was measured by the method of Reed et al. (Reed, L. J. and Mukherjee, B. B., Methods in Enzymology, 13, pp. 55–61, (1969)) by using cells of the strain cultured in LB medium until the logarithmic growth phase. As a result, αKGDH activity of 0.073 (ΔABS/min/mg protein) was detected from the SC17 strain, whereas no αKGDH activity was detected from the SC17sucA strain, and thus it was confirmed that the sucA was deficient as purposed.

(2) Enhancement of L-Glutamic Acid Biosynthetic System of *Enterobacter agglomerans* SC17sucA Strain Subsequently, a citrate synthase gene, a phosphoenolpyruvate carboxylase gene and a glutamate dehydrogenase gene derived from *Escherichia coli* were introduced into the SC17sucA strain.

(i) Preparation of Plasmid Having gltA Gene, ppc Gene and gdhA Gene Derived from *Escherichia coli*

Figure 6:
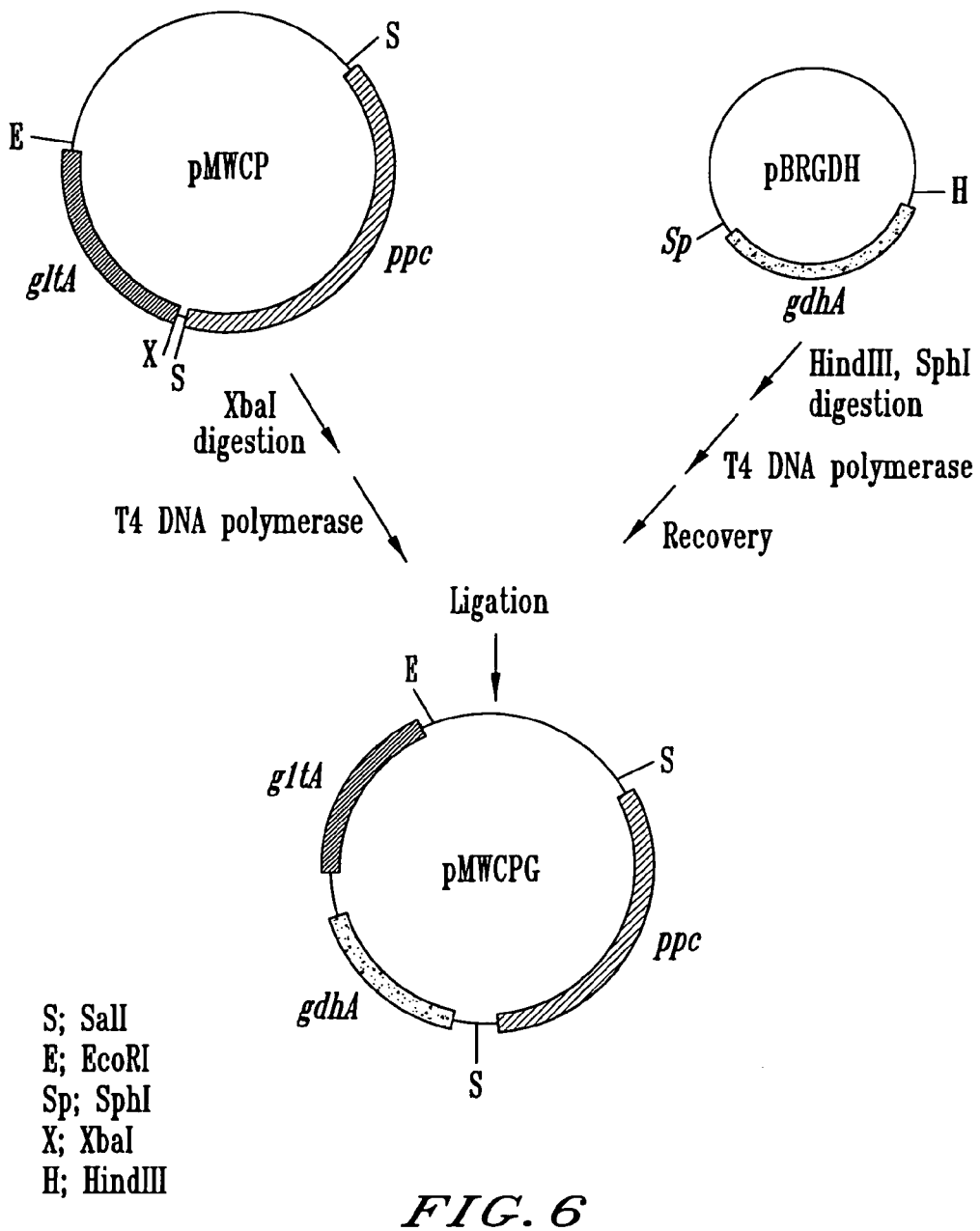
FIG. 6 shows construction of plasmid pMWCPG having a gltA gene, a ppc gene and a gdhA gene.
Figure 7:
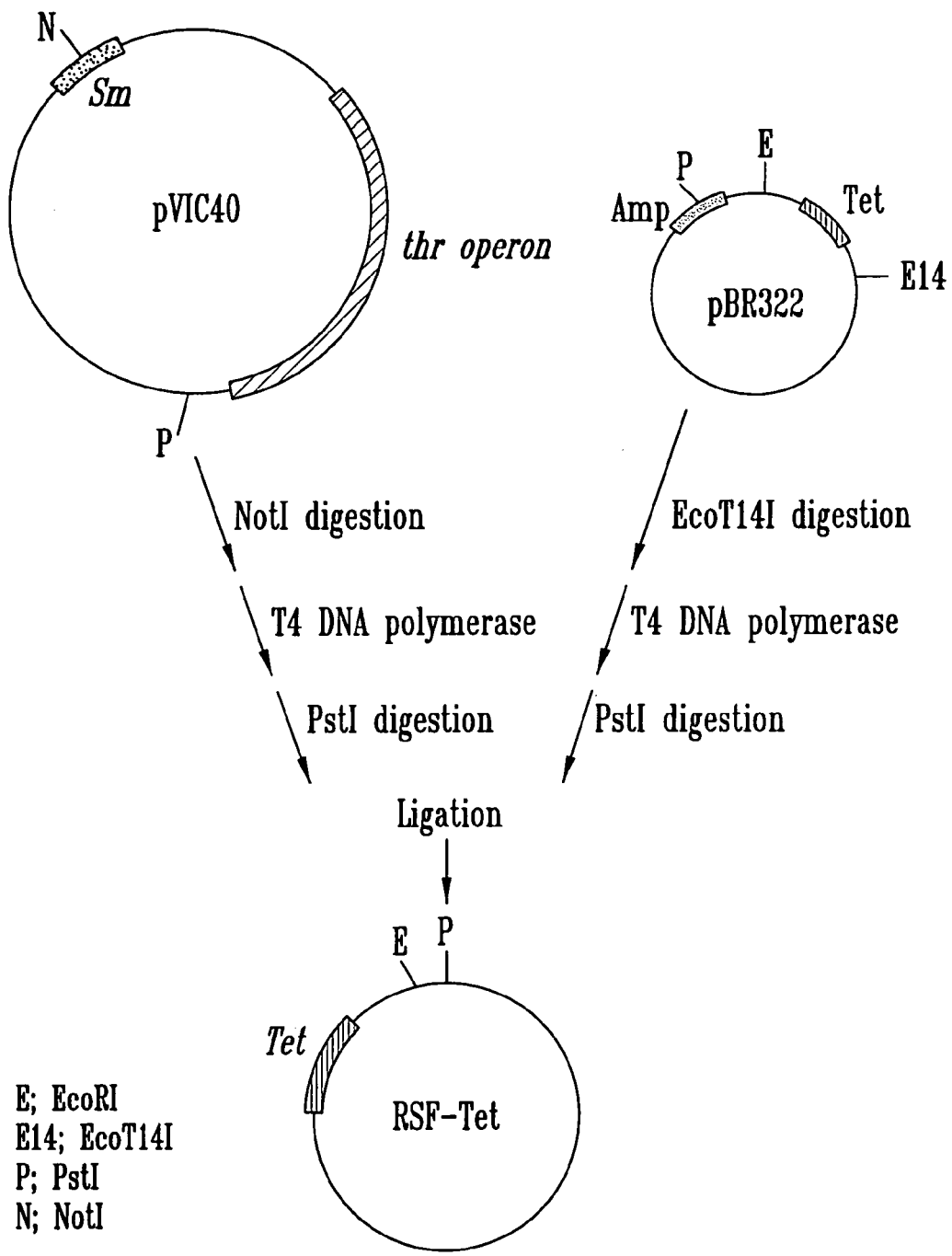
FIG. 7 shows construction of plasmid RSF-Tet having the replication origin of the broad host spectrum plasmid RSF1010 and a tetracycline resistance gene.

The procedures of preparing a plasmid having a gltA gene, a ppc gene and a gdhA gene will be explained by referring to FIGS. 6 and 7.

A plasmid having a gdhA gene derived from *Escherichia coli*, pBRGDH (Japanese Patent Application Laid-open No. 7-203980), was digested with HindIII and SphI, the both ends were blunt-ended by the T4 DNA polymerase treatment, and then the DNA fragment having the gdhA gene was purified and recovered. Separately, a plasmid having a gltA gene and a ppc gene derived from *Escherichia coli*, pMWCP (WO 97/08294), was digested with XbaI, and then the both ends were blunt-ended by using T4 DNA polymerase. This was mixed with the above purified DNA fragment having the gdhA gene and ligated by using T4 ligase to obtain a plasmid pMWCPG, which corresponded to pMWCP further containing the gdhA gene (FIG. 6).

At the same time, the plasmid pVIC40 (Japanese Patent Application Laid-open No. 8-047397) having the replication origin of the broad host spectrum plasmid RSF1010 was digested with NotI, treated with T4 DNA polymerase and digested with PstI. pBR322 was digested with EcoT14I, treated with T4 DNA polymerase and digested with PstI. The both products were mixed and ligated by using T4 ligase to obtain a plasmid RSF-Tet having the replication origin of RSF1010 and a tetracycline resistance gene (FIG. 7).

Figure 8:
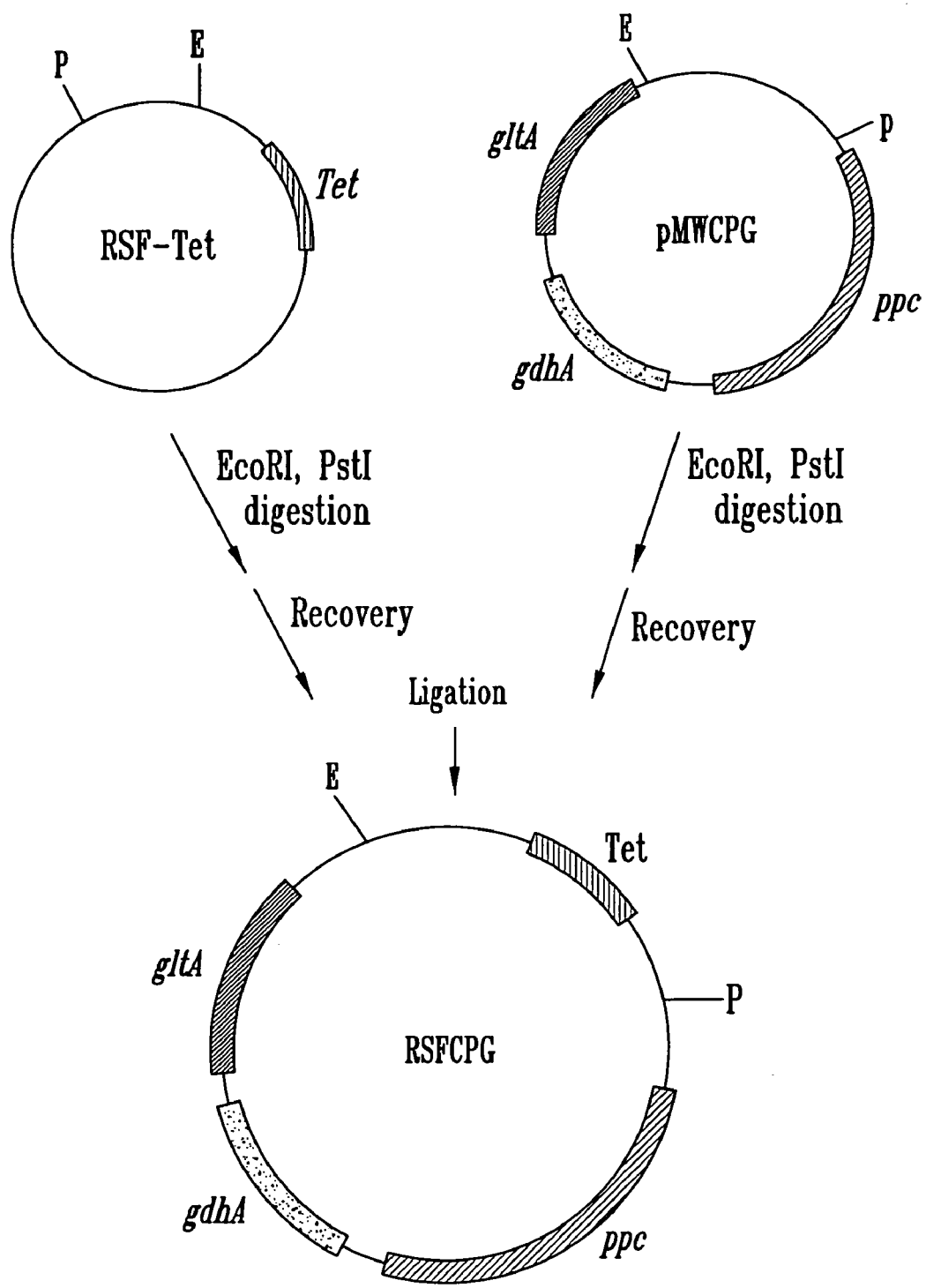
FIG. 8 shows construction of plasmid RSFCPG having the replication origin of the broad host spectrum plasmid RSF1010, a tetracycline resistance gene, a gltA gene, a ppc gene and a gdhA gene.

Subsequently, pMWCPG was digested with EcoRI and PstI, and a DNA fragment having the gltA gene, the ppc gene and the gdhA gene was purified and recovered. RSF-Tet was similarly digested with EcoRI and PstI, and a DNA fragment having the replication origin of RSF1010 was purified and recovered. The both products were mixed and ligated by using T4 ligase to obtain a plasmid RSFCPG, which corresponded to RSF-Tet containing the gltA gene, the ppc gene and the gdhA gene (FIG. 8). It was confirmed that the obtained plasmid RSFCPG expressed the gltA gene, the ppc gene and the gdhA gene, by the complementation of the auxotrophy of the gltA, ppc or gdhA gene deficient strain derived from *Escherichia coli* and measurement of each enzyme activity.

(ii) Preparation of Plasmid Having gltA Gene Derived from *Brevibacterium lactofermentum*

Figure 9:
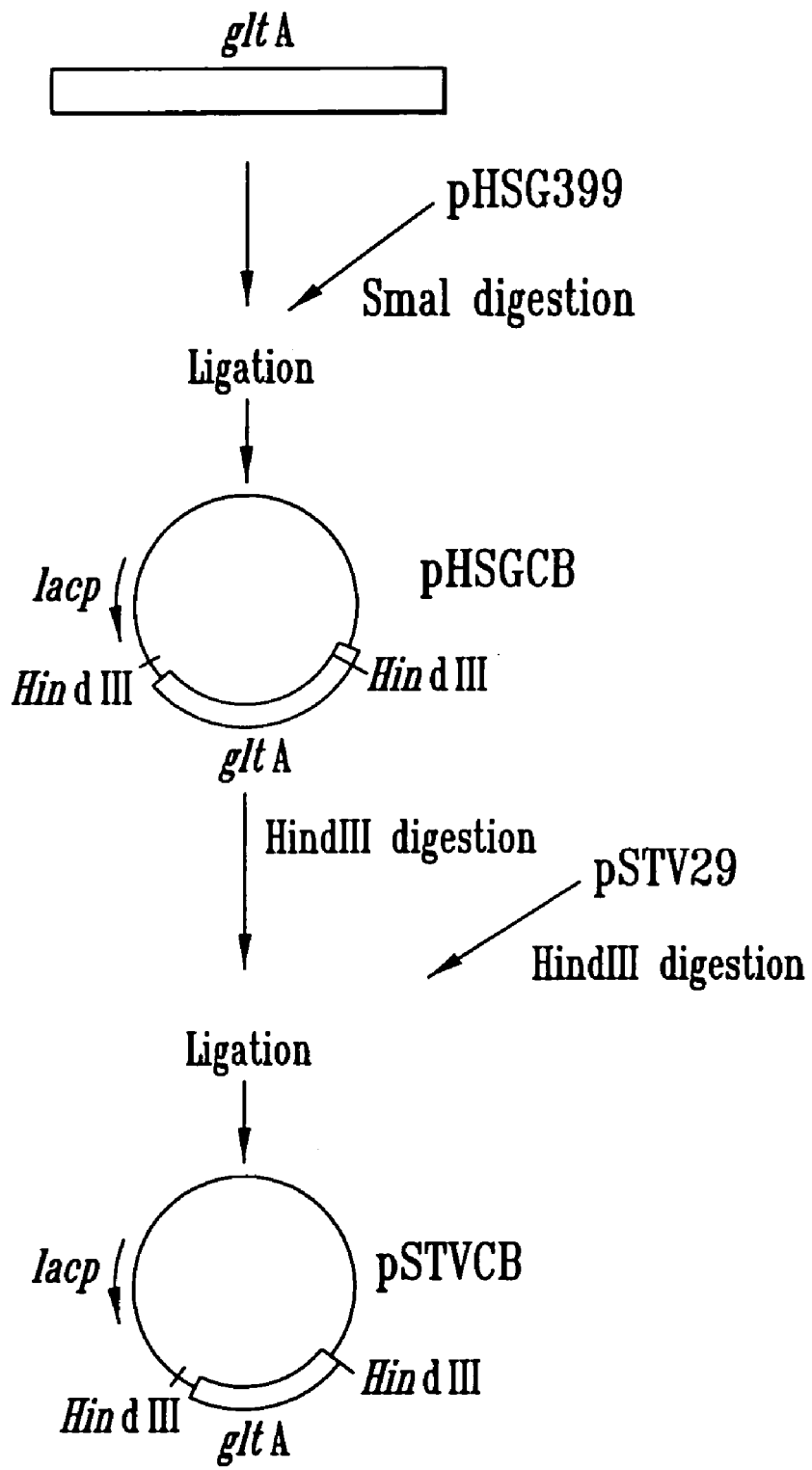
FIG. 9 shows construction of plasmid pSTVCB having a gltA gene.

A plasmid having the gltA gene derived from *Brevibacterium lactofermentum* was constructed as follows. PCR was performed by using the primer DNAs having the nucleotide sequences represented by SEQ ID NOS: 6 and 7, which were prepared based on the nucleotide sequence of the *Corynebacterium glutamicum* gltA gene (Microbiology, 140, pp. 1817–1828 (1994)), and chromosomal DNA of *Brevibacterium* lactofermentum ATCC13869 as a template to obtain a gltA gene fragment of about 3 kb. This fragment inserted into a plasmid pHSG399 (purchased from Takara Shuzo Co., Ltd.) digested with SmaI to obtain a plasmid pHSGCB (FIG. 9). Subsequently, pHSGCB was digested with HindIII, and the excised gltA gene fragment of about 3 kb was inserted into a plasmid pSTV29 (purchased from Takara Shuzo Co., Ltd.) digested with HindIII to obtain a plasmid pSTVCB (FIG. 9). It was confirmed that the obtained plasmid pSTVCB expressed the gltA gene, by measuring the enzyme activity in the *Enterobacter agglomerans* AJ13355 strain.

(iii) Introduction of RSFCPG and pSTVCB into SC17sucA Strain

The *Enterobacter agglomerans* SC17sucA strain was transformed with RSFCPG by electroporation to obtain a transformant SC17sucA/RSFCPG strain having tetracycline resistance. Further, the SC17sucA/RSFCPG strain was transformed with pSTVCB by electroporation to obtain a transformant SC17sucA/RSFCPG+pSTVCB strain having chloramphenicol resistance.

<4> Acquisition of Strain with Improved Resistance to L-Glutamic Acid in Low pH Environment A strain with improved resistance to L-glutamic acid at a high concentration in a low pH environment (hereafter, also referred to as "high-concentration Glu-resistant strain at low pH") was isolated from the *Enterobacter agglomerans* SC17sucA/RSFCPG+pSTVCB strain.

The SC17sucA/RSFCPG+pSTVCB strain was cultured overnight at 30° C. in LBG medium (10 g/L of tryptone, 5 g/L of yeast extract, 10 g/L of NaCl, 5 g/L of glucose), and the cells washed with saline was appropriately diluted and plated on an M9-E medium (4 g/L of glucose, 17 g/L of $Na_2HPO_4.12H_2O$, 3 g/L of $KH_2PO_4$, 0.5 g/L of NaCl, 1 g/L of $NH_4Cl$, 10 mM of $MgSO_4$, 10 µM of $CaCl_2$, 50 mg/L of L-lysine, 50 mg/L of L-methionine, 50 mg/L of DL-diaminopimelic acid, 25 mg/L of tetracycline, 25 mg/L of chloramphenicol, 30 g/L of L-glutamic acid, adjusted to pH 4.5 with aqueous ammonia) plate. The colony emerged after culture at 32° C. for 2 days was obtained as a high-concentration Glu-resistant strain at low pH.

For the obtained strain, growth level in M9-E liquid medium was measured and L-glutamic acid-producing ability was tested in a 50-ml volume large test tube containing 5 ml of L-glutamic acid production test medium (40 g/L of glucose, 20 g/L of $(NH_4)_2SO_4$, 0.5 g/L of $MgSO_4.7H_2O$, 2 g/L of $KH_2PO_4$, 0.5 g/L of NaCl, 0.25 g/L of $CaCl_2.7H_2O$, 0.02 g/L of $FeSO_4.7H_2O$, 0.02 g/L of $MnSO_4.4H_2O$, 0.72 mg/L of $ZnSO_4.2H_2O$, 0.64 mg/L of $CuSO_4.5H_2O$, 0.72 mg/L of $CoCl_2.6H_2O$, 0.4 mg/L of boric acid, 1.2 mg/L of $Na_2MoO_4.2H_2O$, 2 g/L of yeast extract, 200 mg/L of L-lysine hydrochloride, 200 mg/L of L-methionine, 200 mg/L of DL-α,ε-diaminopimelic acid, 25 mg/L of tetracycline hydrochloride, 25 mg/L of chloramphenicol). A strain that exhibited the best growth level and the same L-glutamic acid producing ability as that of its parent strain, the SC17/RSFCPG+pSTVCB strain, was designated as *Enterobacter agglomerans* AJ13601. The AJ13601 strain was deposited at the National Institute of Bioscience and Human-Technology, Agency of Industrial Science and Technology, Ministry of International Trade and Industry (postal code: 305-8566, 1-3, Higashi 1-chome, Tsukuba-shi, Ibaraki, Japan) on Aug. 18, 1999 and received an accession number of FERM P-17516. It was then transferred to an international deposition under the provisions of Budapest Treaty on Jul. 6, 2000 and received an accession number of FERM BP-7207.

<5> Culture of *Enterobacter Agglomerans* AJ13601 Strain for L-Glutamic Acid Production (1)

The *Enterobacter agglomerans* AJ13601 strain was inoculated into a 1-L jar fermenter containing 300 ml of medium containing 40 g/L of glucose, 20 g/L of $(NH_4)_2SO_4$, 0.5 g/L of $MgSO_4.7H_2O$, 2 g/L of $KH_2PO_4$, 0.5 g/L of NaCl, 0.25 g/L of $CaCl_2.7H_2O$, 0.02 g/L of $FeSO_4.7H_2O$, 0.02 g/L of $MnSO_4.4H_2O$, 0.72 mg/L of $ZnSO_4.2H_2O$, 0.64 mg/L of $CuSO_4.5H_2O$, 0.72 mg/L of $CoCl_2.6H_2O$, 0.4 mg/L of boric acid, 1.2 mg/L of Na$_2$MoO$_4$.2H$_2$O, 2 g/L of yeast extract, 200 mg/L of L-lysine hydrochloride, 200 mg/L of L-methionine, 200 mg/L of DL-α,ε-diaminopimelic acid, 25 mg/L of tetracycline hydrochloride and 25 mg/L of chloramphenicol, and cultured at 34° C. and pH 6.0 for 14 hours. The culture pH was controlled by introducing ammonia gas into the medium.

The culture obtained as described above was centrifuged at 5000 rpm for 10 minutes, and the collected cells were inoculated into a 1-L jar fermenter containing 300 ml of medium containing 40 g/L of glucose, 5 g/L of (NH$_4$)$_2$SO$_4$, 1.5 g/L of MgSO$_4$.7H$_2$O, 6 g/L of KH$_2$PO$_4$, 1.5 g/L of NaCl, 0.75 g/L of CaCl$_2$.7H$_2$O, 0.06 g/L of FeSO$_4$.7H$_2$O, 0.06 g/L of MnSO$_4$.4H$_2$O, 2.16 mg/L of ZnSO$_4$.2H$_2$O, 1.92 mg/L of CuSO$_4$.5H$_2$O, 2.16 mg/L of CoCl$_{20}$.6H$_2$O, 1.2 mg/L of boric acid, 3.6 mg/L of Na$_2$MoO$_4$.2H$_2$O, 6 g/L of yeast extract, 600 mg/L of L-lysine hydrochloride, 600 mg/L of L-methionine, 600 mg/L of DL-α,ε-diaminopimelic acid, 25 mg/L of tetracycline hydrochloride and 25 mg/L of chloramphenicol and cultured at 34° C. and pH 4.5 to perform culture for L-glutamic acid production. The culture pH was controlled by introducing ammonia gas into the medium. As the initially added glucose was depleted, 600 g/L of glucose was continuously added.

As a result of the culture for L-glutamic acid production performed for 50 hours as described above, a substantial amount of L-glutamic acid crystals were precipitated in the jar fermenter. Table 1 shows the concentration of L-glutamic acid dissolved in the culture broth at that time and the L-glutamic acid concentration measured by dissolving the crystals in 2 M potassium hydroxide. L-Glutamic acid crystals were collected from the culture by decantation after the culture was left stood.

TABLE 1

| | |
|---|---|
| Concentration of L-glutamic acid dissolved in culture broth | 51 g/L |
| Amount of L-glutamic acid precipitated as crystals | 67 g/L |
| Concentration of L-glutamic acid measured by dissolving crystals | 118 g/L |

<6> Culture of *Enterobacter Agglomerans* AJ13601 Strain for L-Glutamic Acid Production (2)

The following experiment was performed in order to confirm that the *Enterobacter agglomerans* AJ13601 strain still had L-glutamic acid-producing ability even under the condition that L-glutamic acid crystals were present.

The *Enterobacter agglomerans* AJ13601 strain was inoculated into a 1-L jar fermenter containing 300 ml of medium containing 40 g/L of glucose, 20 g/L of (NH$_4$)$_2$SO$_4$, 0.5 g/L of MgSO$_4$.7H$_2$O, 2 g/L of KH$_2$PO$_4$, 0.5 g/L of NaCl, 0.25 g/L of CaCl$_2$.7H$_2$O, 0.02 g/L of FeSO$_4$.7H$_2$O, 0.02 g/L of MnSO$_4$.4H$_2$O, 0.72 mg/L of ZnSO$_4$.2H$_2$O, 0.64 mg/L of CuSO$_4$.5H$_2$O, 0.72 mg/L of CoCl$_2$.6H$_2$O, 0.4 mg/L of boric acid, 1.2 mg/L of Na$_2$MoO$_4$.2H$_2$O, 2 g/L of yeast extract, 200 mg/L of L-lysine hydrochloride, 200 mg/L of L-methionine, 200 mg/L of DL-α,ε-diaminopimelic acid, 25 mg/L of tetracycline hydrochloride and 25 mg/L of chloramphenicol, and cultured at 34° C. at pH 6.0 for 14 hours. The culture pH was controlled by bubbling the medium with ammonia gas. The culture obtained as described above was centrifuged at 5000 rpm for 10 minutes, and then the collected cells were cultured in a medium where L-glutamic acid was present as crystals. The used medium contained 40 g/L of glucose, 5 g/L of (NH$_4$)$_2$SO$_4$, 1.5 g/L of MgSO$_4$.7H$_2$O, 6 g/L of KH$_2$PO$_4$, 1.5 g/L of NaCl, 0.75 g/L of CaCl$_2$.7H$_2$O, 0.06 g/L of FeSO$_4$.7H$_2$O, 0.06 g/L of MnSO$_4$.4H$_2$O, 2.16 mg/L of ZnSO$_4$.2H$_2$O, 1.92 mg/L of CuSO$_4$.5H$_2$O, 2.16 mg/L of CoCl$_2$.6H$_2$O, 1.2 mg/L of boric acid, 3.6 mg/L of Na$_2$MoO$_4$.2H$_2$O, 6 g/L of yeast extract, 600 mg/L of L-lysine hydrochloride, 600 mg/L of L-methionine, 600 mg/L of DL-α,ε-diaminopimelic acid, 25 mg/L of tetracycline hydrochloride and 25 mg/L of chloramphenicol and L-glutamic acid crystals were added to 40 g/L. The cells were inoculated in a 1-L jar fermenter containing 300 ml of this medium and cultured at 34° C. and pH 4.3 to perform culture for L-glutamic acid production. The culture pH was controlled by introducing ammonia gas into the medium. As the initially added glucose was depleted, 600 g/L of glucose was continuously added. In this medium, only 39 g/L of the added L-glutamic acid was dissolved at pH 4.3 and the remaining 1 g/L was present as crystals.

As a result of the culture for L-glutamic acid production performed for 53 hours as described above, a substantial amount of L-glutamic acid crystals were precipitated in the jar fermenter. Table 2 shows the concentration of L-glutamic acid dissolved in the culture broth, the amount of L-glutamic acid present as crystals at that time and the L-glutamic acid concentration measured by dissolving the crystals in 2MKOH solution. L-Glutamic acid crystals were collected from the culture by decantation after the culture was left stood. The results showed that the *Enterobacter agglomerans* AJ13601 strain accumulated L-glutamic acid and precipitated crystals thereof even under the condition that L-glutamic acid crystals were present.

TABLE 2

| | |
|---|---|
| Concentration of L-glutamic acid dissolved in culture broth | 39 g/L |
| Amount of L-glutamic acid precipitated as crystals | 119 g/L |
| Concentration of L-glutamic acid measured by dissolving crystals | 158 g/L |
| Amount of L-glutamic acid crystals newly produced by main culture | 118 g/L |

<7> Culture of *Enterobacter agglomerans* AJ13601 Strain for L-Glutamic Acid Production (3)

The *Enterobacter agglomerans* AJ13601 strain can grow not only at an acidic pH, but also at a neutral pH. Therefore, it was confirmed as follows that L-glutamic acid crystals could also be precipitated by starting the culture at a neutral pH and allowing production of L-glutamic acid during the culture so that pH of the culture should spontaneously be lowered.

Cells of one plate (8.5 cm in diameter) of the *Enterobacter agglomerans* AJ13601 strain, cultured on LBG agar medium (10 g/ of L tryptone, 5 g/L of yeast extract, 10 g/L of NaCl, 5 g/L of glucose, 15 g/L of agar) containing 25 mg/L of tetracycline hydrochloride and 25 mg/L of chloramphenicol at 30° C. for 14 hours, were inoculated into a 1-L jar fermenter containing 300 ml of medium containing 40 g/L of glucose, 5 g/L of (NH$_4$)$_2$SO$_4$, 1.5 g/L of MgSO$_4$.7H$_2$O, 6 g/L of KH$_2$PO$_4$, 1.5 g/L of NaCl, 0.75 g/L of CaCl$_2$.7H$_2$O, 0.06 g/L of FeSO$_4$.7H$_2$O, 0.06 g/L of MnSO$_4$.4H$_2$O, 2.16 mg/L of ZnSO$_4$.2H$_2$O, 1.92 mg/L of CuSO$_4$.5H$_2$O, 2.16 mg/L of CoCl$_2$.6H$_2$O., 1.2 mg/L of boric acid, 3.6 mg/L of Na$_2$MoO$_4$.2H$_2$O, 6 g/L of yeast extract, 600 mg/L of L-lysine hydrochloride, 600 mg/L of L-methionine, 600 mg/L of DL-α,ε-diaminopimelic acid, 25 mg/L of tetracycline hydrochloride and 25 mg/L of chloramphenicol and the culture was started at 34° C. and pH 7.0. The culture pH was controlled by introducing ammonia gas into the medium. As the initially added glucose was depleted, 600 g/L of glucose was continuously added.

As L-glutamic acid is accumulated, pH lowers spontaneously. The amount of the introduced ammonia gas was adjusted so that pH should be gradually lowered from 7.0 to 4.5 during the period between 15 hours and 24 hours after the start of the culture, and 24 hours after the start of the culture, pH became 4.5. Afterward, cultivation was continued for 12 hours.

As a result of the culture for L-glutamic acid production conducted for 36 hours as described above, a substantial amount of L-glutamic acid crystals were precipitated in the jar fermenter. Table 3 shows the concentration of L-glutamic acid dissolved in the culture broth, the amount of L-glutamic acid present as crystals at that time and the L-glutamic acid concentration measured by dissolving the crystals in 2 MKOH solution. L-Glutamic acid crystals were collected from the culture by decantation after the culture was left stood.

TABLE 3

| | |
|---|---|
| Concentration of L-glutamic acid dissolved in culture broth | 45 g/L |
| Amount of L-glutamic acid precipitated as crystals | 31 g/L |
| Concentration of L-glutamic acid measured by dissolving crystals | 76 g/L |

What is claimed is:

1. A method for producing L-glutamic acid by fermentation, which comprises culturing an isolated microorganism in a liquid medium of which pH is adjusted to the pH at which L-glutamic acid is precipitated, to produce and accumulate L-glutamic acid and precipitate L-glutamic acid in the medium, wherein said microorganism can metabolize a carbon source at a specific pH in a liquid medium containing the carbon source and L-glutamic acid at a saturation concentration, and has the ability to accumulate L-glutamic acid in an amount exceeding the amount corresponding to the saturation concentration in the liquid medium at the pH, wherein said microorganism is Enterobacter agglomerans, and wherein said microorganism has at least one of the following characteristics: (a) the microorganism has increased activity, as compared to a corresponding wild-type microorganism, of an enzyme that catalyzes a reaction for biosynthesis of L-glutamic acid; and (b) the microorganism has decreased activity, as compared to a corresponding wild-type microorganism, or deficient activity of an enzyme that catalyzes a reaction of a pathway branching from a biosynthetic pathway of L-glutamic acid and producing a compound other than L-glutamic acid.

2. The method according to claim 1, wherein said microorganism can grow in the liquid medium.

3. The method according to claim 1, wherein the pH is not more than 5.0.

4. The method according to claim 1, wherein in said microorganism an activity of at least one enzyme selected from the group consisting of citrate synthase, phosphoenolpyruvate carboxylase and glutamate dehydrogenase, is increased.

5. The method according to claim 1, wherein in said microorganism the enzyme that catalyzes the reaction of the pathway branching from the biosynthetic pathway of L-glutamic acid and producing the compound other than L-glutamic acid is α-ketoglutarate dehydrogenase.

6. The method according to claim 1, wherein said microorganism has a mutation that causes less extracellular secretion of a viscous material compared with a wild strain when cultured in a medium containing a saccharide.

* * * * *

SEQUENCE LISTING

```
<160> NUMBER OF SEQ ID NOS: 12

<210> SEQ ID NO 1
<211> LENGTH: 4556
<212> TYPE: DNA
<213> ORGANISM: Enterobacter agglomerans
<220> FEATURE:
<221> NAME/KEY: CDS
<222> LOCATION: (2)..(121)
<220> FEATURE:
<221> NAME/KEY: CDS
<222> LOCATION: (322)..(3129)
<220> FEATURE:
<221> NAME/KEY: CDS
<222> LOCATION: (3145)..(4368)
<220> FEATURE:
<221> NAME/KEY: CDS
<222> LOCATION: (4437)..(4556)

<400> SEQUENCE: 1 t gca ttc agc gtt ttc cgc tgt cac agc atc atg aac tgt gta agt gtt        49
  Ala Phe Ser Val Phe Arg Cys His Ser Ile Met Asn Cys Val Ser Val
  1               5                  10                  15 tgt cct aaa ggg cta aac ccg acg cgc gct atc ggc cac att aag tcg        97
Cys Pro Lys Gly Leu Asn Pro Thr Arg Ala Ile Gly His Ile Lys Ser
              20                  25                  30 atg ctg ctg caa cgc agc gcg tag ttataccacc gggaacctca ggttcccgt       151
Met Leu Leu Gln Arg Ser Ala
              35 attttacgga agcctctgta aacgcggtcc caaccacgtt tacaaaggtt cccttacggg      211 ccgggcgcgc gctgcgcaca gtgctcgtat cgctgaactc actacggcaa accgcgaaag     271 cggcaacaaa tgaaacctca aaaagcata acattgctta agggatcaca atg cag         327
                                                       Met Gln
                                                       40 aac agc gcg atg aag ccc tgg ctg gac tcc tcc tgg ctg gcc ggc gcg        375
Asn Ser Ala Met Lys Pro Trp Leu Asp Ser Ser Trp Leu Ala Gly Ala
                 45                  50                  55 aat cag tct tac ata gag caa ctc tat gag gat ttc ctg acc gat cct        423
Asn Gln Ser Tyr Ile Glu Gln Leu Tyr Glu Asp Phe Leu Thr Asp Pro
             60                  65                  70 gac tct gtg gat gca gtg tgg cgc tcg atg ttc caa cag tta cca ggc        471
Asp Ser Val Asp Ala Val Trp Arg Ser Met Phe Gln Gln Leu Pro Gly
         75                  80                  85 acg gga gtg aaa cct gag cag ttc cac tcc gca act cgc gaa tat ttc        519
Thr Gly Val Lys Pro Glu Gln Phe His Ser Ala Thr Arg Glu Tyr Phe
```

-continued

```
                  90                    95                   100                   105
cgt cgc ctg gcg aaa gac gca tct cgt tac acc tcc tca gtt acc gat         567
Arg Arg Leu Ala Lys Asp Ala Ser Arg Tyr Thr Ser Ser Val Thr Asp
                110                   115                   120 ccg gca acc aac tcc aaa caa gtg aaa gtg ctg cag ctg att aac gcg         615
Pro Ala Thr Asn Ser Lys Gln Val Lys Val Leu Gln Leu Ile Asn Ala
            125                   130                   135 ttt cgt ttc cgc gga cat cag gaa gca aat ctc gat ccg ctt ggc ctg         663
Phe Arg Phe Arg Gly His Gln Glu Ala Asn Leu Asp Pro Leu Gly Leu
        140                   145                   150 tgg aaa cag gac cgc gtt gcc gat ctc gat cct gcc ttt cac gat ctg         711
Trp Lys Gln Asp Arg Val Ala Asp Leu Asp Pro Ala Phe His Asp Leu
    155                   160                   165 acc gac gcc gat ttt cag gaa agc ttt aac gta ggt tct ttt gcc att         759
Thr Asp Ala Asp Phe Gln Glu Ser Phe Asn Val Gly Ser Phe Ala Ile
170                   175                   180                   185 ggc aaa gaa acc atg aag ctg gcc gat ctg ttc gac gcg ctg aag cag         807
Gly Lys Glu Thr Met Lys Leu Ala Asp Leu Phe Asp Ala Leu Lys Gln
                190                   195                   200 acc tac tgt ggc tcg att ggt gca gag tat atg cac atc aat aac acc         855
Thr Tyr Cys Gly Ser Ile Gly Ala Glu Tyr Met His Ile Asn Asn Thr
            205                   210                   215 gaa gag aaa cgc tgg atc cag cag cgt atc gaa tcc ggt gcg agc cag         903
Glu Glu Lys Arg Trp Ile Gln Gln Arg Ile Glu Ser Gly Ala Ser Gln
        220                   225                   230 acg tca ttc agt ggc gaa gag aaa aaa ggt ttc ctg aaa gag ctg acc         951
Thr Ser Phe Ser Gly Glu Glu Lys Lys Gly Phe Leu Lys Glu Leu Thr
    235                   240                   245 gcg gca gaa ggg ctg gaa aaa tat ctg ggc gcg aaa ttc ccg ggt gca         999
Ala Ala Glu Gly Leu Glu Lys Tyr Leu Gly Ala Lys Phe Pro Gly Ala
250                   255                   260                   265 aaa cgt ttc tcg ctg gaa ggc ggt gat gcg ctg gtg ccg atg ctg cgc        1047
Lys Arg Phe Ser Leu Glu Gly Gly Asp Ala Leu Val Pro Met Leu Arg
                270                   275                   280 gag atg att cgt cat gcg ggc aaa agc ggc aca cgt gaa gtg gta ctg        1095
Glu Met Ile Arg His Ala Gly Lys Ser Gly Thr Arg Glu Val Val Leu
            285                   290                   295 ggg atg gcg cac cgt ggc cgt ctt aac gta ctg att aac gta ctg ggt        1143
Gly Met Ala His Arg Gly Arg Leu Asn Val Leu Ile Asn Val Leu Gly
        300                   305                   310 aaa aag cca cag gat ctg ttc gac gaa ttc tcc ggt aaa cac aaa gag        1191
Lys Lys Pro Gln Asp Leu Phe Asp Glu Phe Ser Gly Lys His Lys Glu
    315                   320                   325 cat ctg ggc acc ggt gat gtg aag tat cac atg ggc ttc tct tcg gat        1239
His Leu Gly Thr Gly Asp Val Lys Tyr His Met Gly Phe Ser Ser Asp
330                   335                   340                   345 att gaa acc gaa ggt ggt ctg gtg cat ctg gcg ctg gcg ttt aac ccg        1287
Ile Glu Thr Glu Gly Gly Leu Val His Leu Ala Leu Ala Phe Asn Pro
                350                   355                   360 tct cac ctg gaa att gtc agc ccg gtg gtc atg gga tcg gta cgt gca        1335
Ser His Leu Glu Ile Val Ser Pro Val Val Met Gly Ser Val Arg Ala
            365                   370                   375 cgt ctc gat cgt ctg gcc gaa ccg gtc agc aat aaa gtg ttg cct atc        1383
Arg Leu Asp Arg Leu Ala Glu Pro Val Ser Asn Lys Val Leu Pro Ile
        380                   385                   390 acc att cac ggt gat gcg gcg gtg att ggt cag ggc gtg gtt cag gaa        1431
Thr Ile His Gly Asp Ala Ala Val Ile Gly Gln Gly Val Val Gln Glu
    395                   400                   405 acc ctg aac atg tct cag gcg cgc ggc tac gaa gtg ggc ggc acg gta        1479
```

-continued

| | | |
|---|---|---|
| Thr Leu Asn Met Ser Gln Ala Arg Gly Tyr Glu Val Gly Gly Thr Val<br>410                        415                        420                        425 | | |
| cgt atc gtc att aac aac cag gtt ggt ttt acc acc tcc aac ccg aaa<br>Arg Ile Val Ile Asn Asn Gln Val Gly Phe Thr Thr Ser Asn Pro Lys<br>                            430                        435                        440 | 1527 | |
| gat gcg cgt tca acc ccg tac tgt act gac atc ggc aag atg gtg ctg<br>Asp Ala Arg Ser Thr Pro Tyr Cys Thr Asp Ile Gly Lys Met Val Leu<br>                        445                        450                        455 | 1575 | |
| gca ccg att ttc cac gtc aat gct gac gat ccg gaa gcg gtg gcc ttt<br>Ala Pro Ile Phe His Val Asn Ala Asp Asp Pro Glu Ala Val Ala Phe<br>           460                        465                        470 | 1623 | |
| gtt acc cgc ctg gcg ctg gac tat cgc aac acc ttc aaa cgc gat gtg<br>Val Thr Arg Leu Ala Leu Asp Tyr Arg Asn Thr Phe Lys Arg Asp Val<br>                        475                        480                        485 | 1671 | |
| ttt atc gat ctg gtg tgc tat cgc cgt cat ggt cac aac gag gcg gat<br>Phe Ile Asp Leu Val Cys Tyr Arg Arg His Gly His Asn Glu Ala Asp<br>490                        495                        500                        505 | 1719 | |
| gag cca agt gct acc cag ccg ttg atg tac cag aaa atc aaa aag cat<br>Glu Pro Ser Ala Thr Gln Pro Leu Met Tyr Gln Lys Ile Lys Lys His<br>                        510                        515                        520 | 1767 | |
| ccg acg ccg cgt aaa att tac gcc gat cgt ctg gaa ggc gaa ggt gtc<br>Pro Thr Pro Arg Lys Ile Tyr Ala Asp Arg Leu Glu Gly Glu Gly Val<br>                        525                        530                        535 | 1815 | |
| gcg tcg cag gaa gat gcc acc gag atg gtg aac ctg tac cgc gat gcg<br>Ala Ser Gln Glu Asp Ala Thr Glu Met Val Asn Leu Tyr Arg Asp Ala<br>           540                        545                        550 | 1863 | |
| ctc gat gcg ggc gaa tgc gtg gtg ccg gaa tgg cgt ccg atg agc ctg<br>Leu Asp Ala Gly Glu Cys Val Val Pro Glu Trp Arg Pro Met Ser Leu<br>555                        560                        565 | 1911 | |
| cac tcc ttc acg tgg tcg cct tat ctg aac cac gaa tgg gat gag cct<br>His Ser Phe Thr Trp Ser Pro Tyr Leu Asn His Glu Trp Asp Glu Pro<br>570                        575                        580                        585 | 1959 | |
| tat ccg gca cag gtt gac atg aaa cgc ctg aag gaa ctg gca ttg cgt<br>Tyr Pro Ala Gln Val Asp Met Lys Arg Leu Lys Glu Leu Ala Leu Arg<br>                        590                        595                        600 | 2007 | |
| atc agc cag gtc cct gag cag att gaa gtg cag tcg cgc gtg gcc aag<br>Ile Ser Gln Val Pro Glu Gln Ile Glu Val Gln Ser Arg Val Ala Lys<br>                        605                        610                        615 | 2055 | |
| atc tat aac gat cgc aag ctg atg gcc gaa ggc gag aaa gcg ttc gac<br>Ile Tyr Asn Asp Arg Lys Leu Met Ala Glu Gly Glu Lys Ala Phe Asp<br>           620                        625                        630 | 2103 | |
| tgg ggc ggt gcc gag aat ctg gcg tac gcc acg ctg gtg gat gaa ggt<br>Trp Gly Gly Ala Glu Asn Leu Ala Tyr Ala Thr Leu Val Asp Glu Gly<br>635                        640                        645 | 2151 | |
| att ccg gtt cgc ctc tcg ggt gaa gac tcc ggt cgt gga acc ttc ttc<br>Ile Pro Val Arg Leu Ser Gly Glu Asp Ser Gly Arg Gly Thr Phe Phe<br>650                        655                        660                        665 | 2199 | |
| cat cgc cac gcg gtc gtg cac aac cag gct aac ggt tca acc tat acg<br>His Arg His Ala Val Val His Asn Gln Ala Asn Gly Ser Thr Tyr Thr<br>                        670                        675                        680 | 2247 | |
| ccg ctg cac cat att cat aac agc cag ggc gag ttc aaa gtc tgg gat<br>Pro Leu His His Ile His Asn Ser Gln Gly Glu Phe Lys Val Trp Asp<br>           685                        690                        695 | 2295 | |
| tcg gtg ctg tct gaa gaa gcg gtg ctg gcg ttt gaa tac ggt tac gcc<br>Ser Val Leu Ser Glu Glu Ala Val Leu Ala Phe Glu Tyr Gly Tyr Ala<br>                        700                        705                        710 | 2343 | |
| acg gct gag ccg cgc gtg ctg acc atc tgg gaa gcg cag ttt ggt gac<br>Thr Ala Glu Pro Arg Val Leu Thr Ile Trp Glu Ala Gln Phe Gly Asp<br>715                        720                        725 | 2391 | |

```
                                                     -continued ttt gcc aac ggt gct cag gtg gtg att gac cag ttc atc agc tct ggc    2439
Phe Ala Asn Gly Ala Gln Val Val Ile Asp Gln Phe Ile Ser Ser Gly
730                 735                 740                 745 gaa cag aag tgg ggc cgt atg tgt ggc ctg gtg atg ttg ctg ccg cat    2487
Glu Gln Lys Trp Gly Arg Met Cys Gly Leu Val Met Leu Leu Pro His
            750                 755                 760 ggc tac gaa ggt cag gga ccg gaa cac tcc tct gcc gtc ctg gaa cgc    2535
Gly Tyr Glu Gly Gln Gly Pro Glu His Ser Ser Ala Arg Leu Glu Arg
765                 770                 775 tat ctg caa ctt tgc gcc gag cag aac atg cag gtt tgc gtc ccg tcg    2583
Tyr Leu Gln Leu Cys Ala Glu Gln Asn Met Gln Val Cys Val Pro Ser
        780                 785                 790 acg ccg gct cag gtg tat cac atg ctg cgc cgt cag gcg ctg cgc ggg    2631
Thr Pro Ala Gln Val Tyr His Met Leu Arg Arg Gln Ala Leu Arg Gly
    795                 800                 805 atg cgc cgt ccg ctg gtg gtg atg tcg ccg aag tcg ctg tta cgc cat    2679
Met Arg Arg Pro Leu Val Val Met Ser Pro Lys Ser Leu Leu Arg His
810                 815                 820                 825 cca ctg gcg atc tcg tcg ctg gat gaa ctg gca aac ggc agt ttc cag    2727
Pro Leu Ala Ile Ser Ser Leu Asp Glu Leu Ala Asn Gly Ser Phe Gln
            830                 835                 840 ccg gcc att ggt gag atc gac gat ctg gat ccg cag ggc gtg aaa cgc    2775
Pro Ala Ile Gly Glu Ile Asp Asp Leu Asp Pro Gln Gly Val Lys Arg
845                 850                 855 gtc gtg ctg tgc tcc ggt aag gtt tac tac gat ctg ctg gaa cag cgt    2823
Val Val Leu Cys Ser Gly Lys Val Tyr Tyr Asp Leu Leu Glu Gln Arg
        860                 865                 870 cgt aaa gac gag aaa acc gat gtt gcc atc gtg cgc atc gaa cag ctt    2871
Arg Lys Asp Glu Lys Thr Asp Val Ala Ile Val Arg Ile Glu Gln Leu
    875                 880                 885 tac ccg ttc ccg cat cag gcg gta cag gaa gca ttg aaa gcc tat tct    2919
Tyr Pro Phe Pro His Gln Ala Val Gln Glu Ala Leu Lys Ala Tyr Ser
890                 895                 900                 905 cac gta cag gac ttt gtc tgg tgc cag gaa gag cct ctg aac cag ggc    2967
His Val Gln Asp Phe Val Trp Cys Gln Glu Glu Pro Leu Asn Gln Gly
            910                 915                 920 gcc tgg tac tgt agc cag cat cat ttc cgt gat gtc gtg ccg ttt ggt    3015
Ala Trp Tyr Cys Ser Gln His His Phe Arg Asp Val Val Pro Phe Gly
925                 930                 935 gcc acc ctg cgt tat gca ggt cgc ccg gca tcg gct tct ccg gcc gtg    3063
Ala Thr Leu Arg Tyr Ala Gly Arg Pro Ala Ser Ala Ser Pro Ala Val
        940                 945                 950 ggt tat atg tcc gta cac caa caa cag caa gac ctg gtt aat gac         3111
Gly Tyr Met Ser Val His Gln Gln Gln Gln Asp Leu Val Asn Asp
    955                 960                 965 gca ctg aac gtc aat taa ttaaaaggaa agata atg agt agc gta gat att    3162
Ala Leu Asn Val Asn                      Met Ser Ser Val Asp Ile
970                                      975                 980 ctc gtt ccc gac ctg cct gaa tcg gtt gca gat gcc aca gta gca acc    3210
Leu Val Pro Asp Leu Pro Glu Ser Val Ala Asp Ala Thr Val Ala Thr
            985                 990                 995 tgg cac aag aaa  cca ggc gat gca gtc  agc cgc gat gaa gtc  atc     3255
Trp His Lys Lys Pro Gly Asp Ala Val  Ser Arg Asp Glu Val  Ile
                1000                1005                1010 gtc gaa att gaa  act gac aaa gtc gtg  ctg gaa gtg ccg gca  tct     3300
Val Glu Ile Glu Thr Asp Lys Val Val  Leu Glu Val Pro Ala  Ser
                1015                1020                1025 gcc gat ggc gtg  ctg gaa gcc gtg ctg  gaa gac gaa ggg gca  acc     3345
Ala Asp Gly Val Leu Glu Ala Val Leu  Glu Asp Glu Gly Ala  Thr
                1030                1035                1040
```

```
gtt acg tcc cgc cag atc ctg ggt cgc ctg aaa gaa ggc aac agt         3390
Val Thr Ser Arg Gln Ile Leu Gly Arg Leu Lys Glu Gly Asn Ser
        1045                1050                1055 gcg ggt aaa gaa agc agt gcc aaa gcg gaa agc aat gac acc acg         3435
Ala Gly Lys Glu Ser Ser Ala Lys Ala Glu Ser Asn Asp Thr Thr
        1060                1065                1070 cca gcc cag cgt cag aca gcg tcg ctt gaa gaa gag agc agc gat         3480
Pro Ala Gln Arg Gln Thr Ala Ser Leu Glu Glu Glu Ser Ser Asp
        1075                1080                1085 gcg ctc agc ccg gcg atc cgt cgc ctg att gcg gag cat aat ctt         3525
Ala Leu Ser Pro Ala Ile Arg Arg Leu Ile Ala Glu His Asn Leu
        1090                1095                1100 gac gct gcg cag atc aaa ggc acc ggc gta ggc gga cgt tta acg         3570
Asp Ala Ala Gln Ile Lys Gly Thr Gly Val Gly Gly Arg Leu Thr
        1105                1110                1115 cgt gaa gac gtt gaa aaa cat ctg gcg aac aaa ccg cag gct gag         3615
Arg Glu Asp Val Glu Lys His Leu Ala Asn Lys Pro Gln Ala Glu
        1120                1125                1130 aaa gcc gcc gcg cca gcg gcg ggt gca gca acg gct cag cag cct         3660
Lys Ala Ala Ala Pro Ala Ala Gly Ala Ala Thr Ala Gln Gln Pro
        1135                1140                1145 gtt gcc aac cgc agc gaa aaa cgt gtt ccg atg acg cgt tta cgt         3705
Val Ala Asn Arg Ser Glu Lys Arg Val Pro Met Thr Arg Leu Arg
        1150                1155                1160 aag cgc gtc gcg gag cgt ctg ctg gaa gcc aag aac agc acc gcc         3750
Lys Arg Val Ala Glu Arg Leu Leu Glu Ala Lys Asn Ser Thr Ala
        1165                1170                1175 atg ttg acg acc ttc aac gaa atc aac atg aag ccg att atg gat         3795
Met Leu Thr Thr Phe Asn Glu Ile Asn Met Lys Pro Ile Met Asp
        1180                1185                1190 ctg cgt aag cag tac ggc gat gcg ttc gag aag cgt cac ggt gtg         3840
Leu Arg Lys Gln Tyr Gly Asp Ala Phe Glu Lys Arg His Gly Val
        1195                1200                1205 cgt ctg ggc ttt atg tct ttc tac atc aag gcc gtg gtc gaa gcg         3885
Arg Leu Gly Phe Met Ser Phe Tyr Ile Lys Ala Val Val Glu Ala
        1210                1215                1220 ctg aag cgt tat cca gaa gtc aac gcc tct atc gat ggc gaa gac         3930
Leu Lys Arg Tyr Pro Glu Val Asn Ala Ser Ile Asp Gly Glu Asp
        1225                1230                1235 gtg gtg tac cac aac tat ttc gat gtg agt att gcc gtc tct acg         3975
Val Val Tyr His Asn Tyr Phe Asp Val Ser Ile Ala Val Ser Thr
        1240                1245                1250 cca cgc gga ctg gtg acg cct gtc ctg cgt gac gtt gat gcg ctg         4020
Pro Arg Gly Leu Val Thr Pro Val Leu Arg Asp Val Asp Ala Leu
        1255                1260                1265 agc atg gct gac atc gag aag aaa att aaa gaa ctg gca gtg aaa         4065
Ser Met Ala Asp Ile Glu Lys Lys Ile Lys Glu Leu Ala Val Lys
        1270                1275                1280 ggc cgt gac ggc aag ctg acg gtt gac gat ctg acg ggc ggt aac         4110
Gly Arg Asp Gly Lys Leu Thr Val Asp Asp Leu Thr Gly Gly Asn
        1285                1290                1295 ttt acc atc acc aac ggt ggt gtg ttc ggt tcg ctg atg tct acg         4155
Phe Thr Ile Thr Asn Gly Gly Val Phe Gly Ser Leu Met Ser Thr
        1300                1305                1310 cca atc atc aac ccg cca cag agc gcg att ctg ggc atg cac gcc         4200
Pro Ile Ile Asn Pro Pro Gln Ser Ala Ile Leu Gly Met His Ala
        1315                1320                1325 att aaa gat cgt cct atg gcg gtc aat ggt cag gtt gtg atc ctg         4245
Ile Lys Asp Arg Pro Met Ala Val Asn Gly Gln Val Val Ile Leu
```

```
                  1330                1335                1340
cca atg atg tac   ctg gct ctc tcc tac gat cac cgt tta atc gat    4290
Pro Met Met Tyr   Leu Ala Leu Ser Tyr Asp His Arg Leu Ile Asp
            1345                1350                1355 ggt cgt gaa tct   gtc ggc tat ctg gtc gcg gtg aaa gag atg ctg    4335
Gly Arg Glu Ser   Val Gly Tyr Leu Val Ala Val Lys Glu Met Leu
            1360                1365                1370 gaa gat ccg gcg   cgt ctg ctg ctg gat gtc tga ttcatcactg         4378
Glu Asp Pro Ala   Arg Leu Leu Leu Asp Val
            1375                1380 ggcacgcgtt gcgtgcccaa tctcaatact cttttcagat ctgaatggat agaacatc  4436 atg aac tta cac   gaa tac cag gct aaa cag ctg ttt gca cgg tat    4481
Met Asn Leu His   Glu Tyr Gln Ala Lys Gln Leu Phe Ala Arg Tyr
            1385                1390                1395 ggc atg cca gca   ccg acc ggc tac gcc tgt act aca cca cgt gaa    4526
Gly Met Pro Ala   Pro Thr Gly Tyr Ala Cys Thr Thr Pro Arg Glu
            1400                1405                1410 gca gaa gaa gcg   gca tcg aaa atc ggt gca                        4556
Ala Glu Glu Ala   Ala Ser Lys Ile Gly Ala
            1415                1420

<210> SEQ ID NO 2
<211> LENGTH: 39
<212> TYPE: PRT
<213> ORGANISM: Enterobacter agglomerans

<400> SEQUENCE: 2

Ala Phe Ser Val Phe Arg Cys His Ser Ile Met Asn Cys Val Ser Val
1               5                   10                  15

Cys Pro Lys Gly Leu Asn Pro Thr Arg Ala Ile Gly His Ile Lys Ser
            20                  25                  30

Met Leu Leu Gln Arg Ser Ala
        35

<210> SEQ ID NO 3
<211> LENGTH: 935
<212> TYPE: PRT
<213> ORGANISM: Enterobacter agglomerans

<400> SEQUENCE: 3

Met Gln Asn Ser Ala Met Lys Pro Trp Leu Asp Ser Ser Trp Leu Ala
1               5                   10                  15

Gly Ala Asn Gln Ser Tyr Ile Glu Gln Leu Tyr Glu Asp Phe Leu Thr
            20                  25                  30

Asp Pro Asp Ser Val Asp Ala Val Trp Arg Ser Met Phe Gln Gln Leu
        35                  40                  45

Pro Gly Thr Gly Val Lys Pro Glu Gln Phe His Ser Ala Thr Arg Glu
    50                  55                  60

Tyr Phe Arg Arg Leu Ala Lys Asp Ala Ser Arg Tyr Thr Ser Ser Val
65                  70                  75                  80

Thr Asp Pro Ala Thr Asn Ser Lys Gln Val Lys Val Leu Gln Leu Ile
                85                  90                  95

Asn Ala Phe Arg Phe Arg Gly His Gln Glu Ala Asn Leu Asp Pro Leu
            100                 105                 110

Gly Leu Trp Lys Gln Asp Arg Val Ala Asp Leu Asp Pro Ala Phe His
        115                 120                 125

Asp Leu Thr Asp Ala Asp Phe Gln Glu Ser Phe Asn Val Gly Ser Phe
    130                 135                 140
```

-continued

```
Ala Ile Gly Lys Glu Thr Met Lys Leu Ala Asp Leu Phe Asp Ala Leu
145                 150                 155                 160

Lys Gln Thr Tyr Cys Gly Ser Ile Gly Ala Glu Tyr Met His Ile Asn
            165                 170                 175

Asn Thr Glu Glu Lys Arg Trp Ile Gln Gln Arg Ile Glu Ser Gly Ala
        180                 185                 190

Ser Gln Thr Ser Phe Ser Gly Glu Lys Lys Gly Phe Leu Lys Glu
    195                 200                 205

Leu Thr Ala Ala Glu Gly Leu Glu Lys Tyr Leu Gly Ala Lys Phe Pro
210                 215                 220

Gly Ala Lys Arg Phe Ser Leu Glu Gly Gly Asp Ala Leu Val Pro Met
225                 230                 235                 240

Leu Arg Glu Met Ile Arg His Ala Gly Lys Ser Gly Thr Arg Glu Val
            245                 250                 255

Val Leu Gly Met Ala His Arg Gly Arg Leu Asn Val Leu Ile Asn Val
            260                 265                 270

Leu Gly Lys Lys Pro Gln Asp Leu Phe Asp Glu Phe Ser Gly Lys His
    275                 280                 285

Lys Glu His Leu Gly Thr Gly Asp Val Lys Tyr His Met Gly Phe Ser
290                 295                 300

Ser Asp Ile Glu Thr Glu Gly Gly Leu Val His Leu Ala Leu Ala Phe
305                 310                 315                 320

Asn Pro Ser His Leu Glu Ile Val Ser Pro Val Met Gly Ser Val
            325                 330                 335

Arg Ala Arg Leu Asp Arg Leu Ala Glu Pro Val Ser Asn Lys Val Leu
            340                 345                 350

Pro Ile Thr Ile His Gly Asp Ala Ala Val Ile Gly Gln Gly Val Val
            355                 360                 365

Gln Glu Thr Leu Asn Met Ser Gln Ala Arg Gly Tyr Glu Val Gly Gly
    370                 375                 380

Thr Val Arg Ile Val Ile Asn Asn Gln Val Gly Phe Thr Thr Ser Asn
385                 390                 395                 400

Pro Lys Asp Ala Arg Ser Thr Pro Tyr Cys Thr Asp Ile Gly Lys Met
            405                 410                 415

Val Leu Ala Pro Ile Phe His Val Asn Ala Asp Asp Pro Glu Ala Val
            420                 425                 430

Ala Phe Val Thr Arg Leu Ala Leu Asp Tyr Arg Asn Thr Phe Lys Arg
            435                 440                 445

Asp Val Phe Ile Asp Leu Val Cys Tyr Arg Arg His Gly His Asn Glu
    450                 455                 460

Ala Asp Glu Pro Ser Ala Thr Gln Pro Leu Met Tyr Gln Lys Ile Lys
465                 470                 475                 480

Lys His Pro Thr Pro Arg Lys Ile Tyr Ala Asp Arg Leu Glu Gly Glu
            485                 490                 495

Gly Val Ala Ser Gln Glu Asp Ala Thr Glu Met Val Asn Leu Tyr Arg
            500                 505                 510

Asp Ala Leu Asp Ala Gly Glu Cys Val Val Pro Glu Trp Arg Pro Met
            515                 520                 525

Ser Leu His Ser Phe Thr Trp Ser Pro Tyr Leu Asn His Glu Trp Asp
    530                 535                 540

Glu Pro Tyr Pro Ala Gln Val Asp Met Lys Arg Leu Lys Glu Leu Ala
545                 550                 555                 560
```

-continued

Leu Arg Ile Ser Gln Val Pro Glu Gln Ile Glu Val Gln Ser Arg Val
             565                 570                 575

Ala Lys Ile Tyr Asn Asp Arg Lys Leu Met Ala Glu Gly Glu Lys Ala
         580                 585                 590

Phe Asp Trp Gly Gly Ala Glu Asn Leu Ala Tyr Ala Thr Leu Val Asp
     595                 600                 605

Glu Gly Ile Pro Val Arg Leu Ser Gly Glu Asp Ser Gly Arg Gly Thr
610                 615                 620

Phe Phe His Arg His Ala Val His Asn Gln Ala Asn Gly Ser Thr
625                 630                 635                 640

Tyr Thr Pro Leu His His Ile His Asn Ser Gln Gly Glu Phe Lys Val
                 645                 650                 655

Trp Asp Ser Val Leu Ser Glu Glu Ala Val Leu Ala Phe Glu Tyr Gly
             660                 665                 670

Tyr Ala Thr Ala Glu Pro Arg Val Leu Thr Ile Trp Glu Ala Gln Phe
         675                 680                 685

Gly Asp Phe Ala Asn Gly Ala Gln Val Val Ile Asp Gln Phe Ile Ser
     690                 695                 700

Ser Gly Glu Gln Lys Trp Gly Arg Met Cys Gly Leu Val Met Leu Leu
705                 710                 715                 720

Pro His Gly Tyr Glu Gly Gln Gly Pro Glu His Ser Ser Ala Arg Leu
                 725                 730                 735

Glu Arg Tyr Leu Gln Leu Cys Ala Glu Gln Asn Met Gln Val Cys Val
             740                 745                 750

Pro Ser Thr Pro Ala Gln Val Tyr His Met Leu Arg Arg Gln Ala Leu
         755                 760                 765

Arg Gly Met Arg Arg Pro Leu Val Val Met Ser Pro Lys Ser Leu Leu
     770                 775                 780

Arg His Pro Leu Ala Ile Ser Ser Leu Asp Glu Leu Ala Asn Gly Ser
785                 790                 795                 800

Phe Gln Pro Ala Ile Gly Glu Ile Asp Asp Leu Asp Pro Gln Gly Val
                 805                 810                 815

Lys Arg Val Val Leu Cys Ser Gly Lys Val Tyr Tyr Asp Leu Leu Glu
             820                 825                 830

Gln Arg Arg Lys Asp Glu Lys Thr Asp Val Ala Ile Val Arg Ile Glu
         835                 840                 845

Gln Leu Tyr Pro Phe Pro His Gln Ala Val Gln Glu Ala Leu Lys Ala
     850                 855                 860

Tyr Ser His Val Gln Asp Phe Val Trp Cys Gln Glu Pro Leu Asn
865                 870                 875                 880

Gln Gly Ala Trp Tyr Cys Ser Gln His His Phe Arg Asp Val Val Pro
                 885                 890                 895

Phe Gly Ala Thr Leu Arg Tyr Ala Gly Arg Pro Ala Ser Ala Ser Pro
             900                 905                 910

Ala Val Gly Tyr Met Ser Val His Gln Gln Gln Gln Asp Leu Val
         915                 920                 925

Asn Asp Ala Leu Asn Val Asn
930                 935

<210> SEQ ID NO 4
<211> LENGTH: 407
<212> TYPE: PRT
<213> ORGANISM: Enterobacter agglomerans

<400> SEQUENCE: 4

```
Met Ser Ser Val Asp Ile Leu Val Pro Asp Leu Pro Glu Ser Val Ala
1               5                   10                  15

Asp Ala Thr Val Ala Thr Trp His Lys Lys Pro Gly Asp Ala Val Ser
            20                  25                  30

Arg Asp Glu Val Ile Val Glu Ile Glu Thr Asp Lys Val Val Leu Glu
        35                  40                  45

Val Pro Ala Ser Ala Asp Gly Val Leu Glu Ala Val Leu Glu Asp Glu
    50                  55                  60

Gly Ala Thr Val Thr Ser Arg Gln Ile Leu Gly Arg Leu Lys Glu Gly
65                  70                  75                  80

Asn Ser Ala Gly Lys Glu Ser Ser Ala Lys Ala Glu Ser Asn Asp Thr
                85                  90                  95

Thr Pro Ala Gln Arg Gln Thr Ala Ser Leu Glu Glu Glu Ser Ser Asp
            100                 105                 110

Ala Leu Ser Pro Ala Ile Arg Arg Leu Ile Ala Glu His Asn Leu Asp
        115                 120                 125

Ala Ala Gln Ile Lys Gly Thr Gly Val Gly Gly Arg Leu Thr Arg Glu
130                 135                 140

Asp Val Glu Lys His Leu Ala Asn Lys Pro Gln Ala Glu Lys Ala Ala
145                 150                 155                 160

Ala Pro Ala Ala Gly Ala Ala Thr Ala Gln Gln Pro Val Ala Asn Arg
                165                 170                 175

Ser Glu Lys Arg Val Pro Met Thr Arg Leu Arg Lys Arg Val Ala Glu
            180                 185                 190

Arg Leu Leu Glu Ala Lys Asn Ser Thr Ala Met Leu Thr Thr Phe Asn
        195                 200                 205

Glu Ile Asn Met Lys Pro Ile Met Asp Leu Arg Lys Gln Tyr Gly Asp
    210                 215                 220

Ala Phe Glu Lys Arg His Gly Val Arg Leu Gly Phe Met Ser Phe Tyr
225                 230                 235                 240

Ile Lys Ala Val Val Glu Ala Leu Lys Arg Tyr Pro Glu Val Asn Ala
                245                 250                 255

Ser Ile Asp Gly Glu Asp Val Val Tyr His Asn Tyr Phe Asp Val Ser
            260                 265                 270

Ile Ala Val Ser Thr Pro Arg Gly Leu Val Thr Pro Val Leu Arg Asp
        275                 280                 285

Val Asp Ala Leu Ser Met Ala Asp Ile Glu Lys Lys Ile Lys Glu Leu
    290                 295                 300

Ala Val Lys Gly Arg Asp Gly Lys Leu Thr Val Asp Asp Leu Thr Gly
305                 310                 315                 320

Gly Asn Phe Thr Ile Thr Asn Gly Gly Val Phe Gly Ser Leu Met Ser
                325                 330                 335

Thr Pro Ile Ile Asn Pro Pro Gln Ser Ala Ile Leu Gly Met His Ala
            340                 345                 350

Ile Lys Asp Arg Pro Met Ala Val Asn Gly Gln Val Val Ile Leu Pro
        355                 360                 365

Met Met Tyr Leu Ala Leu Ser Tyr Asp His Arg Leu Ile Asp Gly Arg
    370                 375                 380

Glu Ser Val Gly Tyr Leu Val Ala Val Lys Glu Met Leu Glu Asp Pro
385                 390                 395                 400

Ala Arg Leu Leu Leu Asp Val
                405
```

```
<210> SEQ ID NO 5
<211> LENGTH: 40
<212> TYPE: PRT
<213> ORGANISM: Enterobacter agglomerans

<400> SEQUENCE: 5
```

Met Asn Leu His Glu Tyr Gln Ala Lys Gln Leu Phe Ala Arg Tyr Gly
1               5                   10                  15

Met Pro Ala Pro Thr Gly Tyr Ala Cys Thr Thr Pro Arg Glu Ala Glu
            20                  25                  30

Glu Ala Ala Ser Lys Ile Gly Ala
        35                  40

```
<210> SEQ ID NO 6
<211> LENGTH: 30
<212> TYPE: DNA
<213> ORGANISM: Artificial Sequence
<220> FEATURE:
<221> NAME/KEY: misc_feature
<223> OTHER INFORMATION: Artificial Sequence: synthetic DNA

<400> SEQUENCE: 6
```
gtcgacaata gccygaatct gttctggtcg                                       30

```
<210> SEQ ID NO 7
<211> LENGTH: 30
<212> TYPE: DNA
<213> ORGANISM: Artificial Sequence
<220> FEATURE:
<221> NAME/KEY: misc_feature
<223> OTHER INFORMATION: Artificial Sequence: synthetic DNA

<400> SEQUENCE: 7
```
aagcttatcg acgctcccct ccccaccgtt                                       30

```
<210> SEQ ID NO 8
<211> LENGTH: 936
<212> TYPE: PRT
<213> ORGANISM: Escherichia coli

<400> SEQUENCE: 8
```

Met Gln Asn Ser Ala Leu Lys Ala Trp Leu Asp Ser Ser Tyr Leu Ser
1               5                   10                  15

Gly Ala Asn Gln Ser Trp Glu Ile Glu Gln Leu Tyr Glu Asp Phe Leu
            20                  25                  30

Thr Asp Pro Asp Ser Val Asp Ala Asn Trp Arg Ser Thr Phe Gln Gln
        35                  40                  45

Leu Pro Gly Thr Gly Val Lys Pro Asp Gln Phe His Ser Gln Thr Arg
    50                  55                  60

Glu Tyr Phe Arg Arg Leu Ala Lys Asp Ala Ser Arg Tyr Ser Ser Thr
65                  70                  75                  80

Ile Ser Asp Pro Asp Thr Asn Val Lys Gln Val Lys Val Leu Gln Leu
                85                  90                  95

Ile Asn Ala Tyr Arg Phe Arg Gly His Gln His Ala Asn Leu Asp Pro
            100                 105                 110

Leu Gly Leu Trp Gln Gln Asp Lys Val Ala Asp Leu Asp Pro Ser Phe
        115                 120                 125

His Asp Leu Thr Glu Ala Asp Phe Gln Glu Thr Phe Asn Val Gly Ser
    130                 135                 140

Phe Ala Ser Gly Lys Glu Thr Met Lys Leu Gly Glu Leu Leu Glu Ala

-continued

```
            145                 150                 155                 160
    Leu Lys Gln Thr Tyr Cys Gly Pro Ile Gly Ala Glu Tyr Met His Ile
                    165                 170                 175

Thr Ser Thr Glu Glu Lys Arg Trp Ile Gln Gln Arg Ile Glu Ser Gly
                    180                 185                 190

Arg Ala Thr Phe Asn Ser Glu Glu Lys Lys Arg Phe Leu Ser Glu Leu
                    195                 200                 205

Thr Ala Ala Glu Gly Leu Glu Arg Tyr Leu Gly Ala Lys Phe Pro Gly
            210                 215                 220

Ala Lys Arg Phe Ser Leu Glu Gly Gly Asp Ala Leu Ile Pro Met Leu
    225                 230                 235                 240

Lys Glu Met Ile Arg His Ala Gly Asn Ser Gly Thr Arg Glu Val Val
                    245                 250                 255

Leu Gly Met Ala His Arg Gly Arg Leu Asn Val Leu Asn Val Leu Gly
                    260                 265                 270

Lys Lys Pro Gln Asp Leu Phe Asp Glu Phe Ala Gly Lys His Lys Glu
                    275                 280                 285

His Leu Gly Thr Gly Asp Val Lys Tyr His Met Gly Phe Ser Ser Asp
            290                 295                 300

Phe Gln Thr Asp Gly Gly Leu Val His Leu Ala Leu Ala Phe Asn Pro
    305                 310                 315                 320

Ser His Leu Glu Ile Val Ser Pro Val Val Ile Gly Ser Val Arg Ala
                    325                 330                 335

Arg Leu Asp Arg Leu Asp Glu Pro Ser Ser Asn Lys Val Leu Pro Ile
                    340                 345                 350

Thr Ile His Gly Asp Ala Ala Val Thr Gly Gln Gly Val Val Gln Glu
                    355                 360                 365

Thr Leu Asn Met Ser Lys Ala Arg Gly Tyr Glu Val Gly Gly Thr Val
            370                 375                 380

Arg Ile Val Ile Asn Asn Gln Val Gly Phe Thr Thr Ser Asn Pro Leu
    385                 390                 395                 400

Asp Ala Arg Ser Thr Pro Tyr Cys Thr Asp Ile Gly Lys Met Val Gln
                    405                 410                 415

Ala Pro Ile Phe His Val Asn Ala Asp Asp Pro Glu Ala Val Ala Phe
                    420                 425                 430

Val Thr Arg Leu Ala Leu Asp Phe Arg Asn Thr Phe Lys Arg Asp Val
            435                 440                 445

Phe Ile Asp Leu Val Ser Tyr Arg Arg His Gly His Asn Asn Glu Ala
    450                 455                 460

Asp Glu Pro Ser Ala Thr Gln Pro Leu Met Tyr Gln Lys Ile Lys Lys
    465                 470                 475                 480

His Pro Thr Pro Arg Lys Ile Tyr Ala Asp Lys Leu Glu Gln Glu Lys
                    485                 490                 495

Val Ala Thr Leu Glu Asp Ala Thr Glu Met Val Asn Leu Tyr Arg Asp
                    500                 505                 510

Ala Leu Asp Ala Gly Asp Cys Val Val Ala Glu Trp Arg Pro Met Asn
            515                 520                 525

Met His Ser Phe Thr Trp Ser Pro Tyr Leu Asn His Glu Trp Asp Glu
            530                 535                 540

Glu Tyr Pro Asn Lys Val Glu Met Lys Arg Leu Gln Glu Leu Ala Lys
    545                 550                 555                 560

Arg Ile Ser Thr Val Pro Glu Ala Val Glu Met Gln Ser Arg Val Ala
                    565                 570                 575
```

```
Lys Ile Tyr Gly Asp Arg Gln Ala Met Ala Ala Gly Glu Lys Leu Phe
            580                 585                 590

Asp Trp Gly Ala Glu Asn Leu Ala Tyr Ala Thr Leu Val Asp Glu
        595                 600                 605

Gly Ile Pro Val Arg Leu Ser Gly Asp Ser Gly Arg Gly Thr Phe
        610                 615                 620

Phe His Arg His Ala Val Ile His Asn Gln Ser Asn Gly Ser Thr Tyr
625                 630                 635                 640

Thr Pro Leu Gln His Ile His Asn Gly Gln Gly Ala Phe Arg Val Trp
                645                 650                 655

Asp Ser Val Leu Ser Glu Ala Val Leu Ala Phe Glu Tyr Gly Tyr
            660                 665                 670

Ala Thr Ala Glu Pro Arg Thr Leu Thr Ile Trp Glu Ala Gln Phe Gly
            675                 680                 685

Asp Phe Ala Asn Gly Ala Gln Val Val Ile Asp Gln Phe Ile Ser Ser
        690                 695                 700

Gly Glu Gln Lys Trp Gly Arg Met Cys Gly Leu Val Met Leu Leu Pro
705                 710                 715                 720

His Gly Tyr Glu Gly Gln Gly Pro Glu His Ser Ser Ala Arg Leu Glu
                725                 730                 735

Arg Tyr Leu Gln Leu Cys Ala Glu Gln Asn Asn Gln Val Cys Val Pro
            740                 745                 750

Ser Thr Pro Ala Gln Val Tyr His Met Leu Arg Arg Gln Ala Leu Arg
        755                 760                 765

Gly Met Arg Arg Pro Leu Val Val Met Ser Pro Lys Ser Leu Leu Arg
770                 775                 780

His Pro Leu Ala Val Ser Ser Leu Glu Glu Leu Ala Asn Gly Thr Phe
785                 790                 795                 800

Leu Pro Ala Ile Gly Glu Ile Asp Glu Leu Asp Pro Lys Gly Val
                805                 810                 815

Lys Arg Val Val Met Cys Ser Ser Gly Lys Val Tyr Tyr Asp Leu Leu
            820                 825                 830

Glu Gln Arg Arg Lys Asn Asn Gln His Asp Val Ala Ile Val Arg Ile
            835                 840                 845

Glu Gln Leu Tyr Pro Phe Pro His Lys Ala Met Gln Glu Val Leu Gln
            850                 855                 860

Gln Phe Ala His Val Lys Asp Phe Val Trp Cys Gln Glu Glu Pro Leu
865                 870                 875                 880

Asn Gln Gly Ala Trp Tyr Cys Ser Gln His His Phe Arg Glu Val Ile
                885                 890                 895

Pro Phe Gly Ala Ser Leu Arg Tyr Ala Gly Arg Pro Ala Ser Ala Ser
            900                 905                 910

Pro Ala Val Gly Tyr Met Ser Val His Gln Lys Gln Gln Gln Asp Leu
            915                 920                 925

Val Asn Asp Ala Leu Asn Val Glu
    930                 935

<210> SEQ ID NO 9
<211> LENGTH: 405
<212> TYPE: PRT
<213> ORGANISM: Escherichia coli

<400> SEQUENCE: 9

Met Ser Ser Val Asp Ile Leu Val Pro Asp Leu Pro Glu Ser Val Ala
```

```
          1               5                   10                  15
Asp Ala Thr Val Ala Thr Trp His Lys Lys Pro Gly Asp Ala Val Val
                    20                  25                  30

Arg Asp Glu Val Leu Val Glu Ile Glu Thr Asp Lys Val Val Leu Glu
                    35                  40                  45

Val Pro Ala Ser Ala Asp Gly Ile Leu Asp Ala Val Leu Glu Asp Glu
                    50                  55                  60

Gly Thr Thr Val Thr Ser Arg Gln Ile Leu Gly Arg Leu Arg Glu Gly
65                          70                  75                  80

Asn Ser Ala Gly Lys Glu Thr Ser Ala Lys Ser Glu Glu Lys Ala Ser
                    85                  90                  95

Thr Pro Ala Gln Arg Gln Gln Ala Ser Leu Glu Glu Gln Asn Asn Asp
                    100                 105                 110

Ala Leu Ser Pro Ala Ile Arg Arg Leu Leu Ala Glu His Asn Leu Asp
                    115                 120                 125

Ala Ser Ala Ile Lys Gly Thr Gly Val Gly Gly Arg Leu Thr Arg Glu
                    130                 135                 140

Asp Val Glu Lys His Leu Ala Lys Ala Pro Ala Lys Glu Ser Ala Pro
145                         150                 155                 160

Ala Ala Ala Ala Pro Ala Ala Gln Pro Ala Leu Ala Ala Arg Ser Glu
                    165                 170                 175

Lys Arg Val Pro Met Thr Arg Leu Arg Lys Arg Val Ala Glu Arg Leu
                    180                 185                 190

Leu Glu Ala Lys Asn Ser Thr Ala Met Leu Thr Thr Phe Asn Glu Val
                    195                 200                 205

Asn Met Lys Pro Ile Met Asp Leu Arg Lys Gln Tyr Gly Glu Ala Phe
                    210                 215                 220

Glu Lys Arg His Gly Ile Arg Leu Gly Phe Met Ser Phe Tyr Val Lys
225                         230                 235                 240

Ala Val Val Glu Ala Leu Lys Arg Tyr Pro Glu Val Asn Ala Ser Ile
                    245                 250                 255

Asp Gly Asp Asp Val Val Tyr His Asn Tyr Phe Asp Val Ser Met Ala
                    260                 265                 270

Val Ser Thr Pro Arg Gly Leu Val Thr Pro Val Leu Arg Asp Val Asp
                    275                 280                 285

Thr Leu Gly Met Ala Asp Ile Glu Lys Lys Ile Lys Glu Leu Ala Val
                    290                 295                 300

Lys Gly Arg Asp Gly Lys Leu Thr Val Glu Asp Leu Thr Gly Gly Asn
305                         310                 315                 320

Phe Thr Ile Thr Asn Gly Gly Val Phe Gly Ser Leu Met Ser Thr Pro
                    325                 330                 335

Ile Ile Asn Pro Pro Gln Ser Ala Ile Leu Gly Met His Ala Ile Lys
                    340                 345                 350

Asp Arg Pro Met Ala Val Asn Gly Gln Val Glu Ile Leu Pro Met Met
                    355                 360                 365

Tyr Leu Ala Leu Ser Tyr Asp His Arg Leu Ile Asp Gly Arg Glu Ser
                    370                 375                 380

Val Gly Phe Leu Val Thr Ile Lys Glu Leu Leu Glu Asp Pro Thr Arg
385                         390                 395                 400

Leu Leu Leu Asp Val
                    405

<210> SEQ ID NO 10
```

```
<211> LENGTH: 41
<212> TYPE: PRT
<213> ORGANISM: Enterobacter agglomerans

<400> SEQUENCE: 10

Met Asn Leu His Glu Tyr Gln Ala Lys Gln Leu Phe Ala Arg Tyr Gly
1               5                   10                  15

Met Pro Ala Pro Thr Gly Tyr Ala Cys Thr Thr Pro Arg Glu Ala Glu
                20                  25                  30

Glu Ala Ala Ser Lys Ile Gly Ala Gly
            35              40

<210> SEQ ID NO 11
<211> LENGTH: 60
<212> TYPE: PRT
<213> ORGANISM: Escherichia coli

<400> SEQUENCE: 11

Met Asn Leu His Glu Tyr Gln Ala Lys Gln Leu Phe Ala Arg Tyr Gly
1               5                   10                  15

Leu Pro Ala Pro Val Gly Tyr Ala Cys Thr Thr Pro Arg Glu Ala Glu
                20                  25                  30

Glu Ala Ala Ser Lys Ile Gly Ala Gly Pro Trp Val Val Lys Cys Gln
            35              40                  45

Val His Ala Gly Gly Arg Gly Lys Ala Gly Gly Val
        50                  55              60

<210> SEQ ID NO 12
<211> LENGTH: 58
<212> TYPE: PRT
<213> ORGANISM: Escherichia coli

<400> SEQUENCE: 12

Phe Leu Ile Asp Ser Arg Asp Thr Glu Thr Ser Arg Leu Asp Gly
1               5                   10                  15

Leu Ser Asp Ala Phe Ser Val Phe Arg Cys His Ser Ile Met Asn Cys
                20                  25                  30

Val Ser Val Cys Pro Lys Gly Leu Asn Pro Thr Arg Ala Ile Gly His
            35              40                  45

Ile Lys Ser Met Leu Leu Gln Arg Asn Ala
        50                  55
```